(12) United States Patent
Junqua et al.

(10) Patent No.: US 8,803,690 B2
(45) Date of Patent: Aug. 12, 2014

(54) CONTEXT DEPENDENT APPLICATION/EVENT ACTIVATION FOR PEOPLE WITH VARIOUS COGNITIVE ABILITY LEVELS

(71) Applicant: Panasonic Corporation of North America, Secaucus, NJ (US)

(72) Inventors: Jean-Claude Junqua, Saratoga, CA (US); Gary David Sasaki, Cupertino, CA (US); Ricardo Teixeira, Cupertino, CA (US); Philippe Morin, San Jose, CA (US)

(73) Assignee: Panasonic Corporation of North America, Secaucus, NJ (US)

( * ) Notice: Subject to any disclaimer, the term of this patent is extended or adjusted under 35 U.S.C. 154(b) by 0 days.

(21) Appl. No.: 13/730,327

(22) Filed: Dec. 28, 2012

(65) Prior Publication Data
US 2013/0176127 A1 Jul. 11, 2013

Related U.S. Application Data

(60) Provisional application No. 61/631,500, filed on Jan. 6, 2012.

(51) Int. Cl.
*G08B 23/00* (2006.01)
*G08B 21/02* (2006.01)

(52) U.S. Cl.
CPC .................................. *G08B 21/0263* (2013.01)
USPC ................ 340/573.1; 340/309.4; 340/539.12; 340/457; 340/522; 340/691.3

(58) Field of Classification Search
CPC .................................................. G08B 21/0263
USPC ............. 340/573.1, 309.4, 539.12, 457, 522, 340/691.3
See application file for complete search history.

(56) References Cited

U.S. PATENT DOCUMENTS

| | | | |
|---|---|---|---|
| 6,442,573 B1 | 8/2002 | Schiller et al. | |
| 7,076,737 B2 | 7/2006 | Abbott et al. | |
| 7,107,346 B2 | 9/2006 | Boyd | |
| 7,224,777 B1 | 5/2007 | Tannenbaum | |
| 7,397,346 B2 * | 7/2008 | Helal et al. | 340/309.16 |
| 7,428,189 B2 * | 9/2008 | Hubicki | 368/10 |
| 2011/0070835 A1 | 3/2011 | Borras et al. | |
| 2011/0221568 A1 | 9/2011 | Giobbi | |
| 2011/0227739 A1 | 9/2011 | Gilham et al. | |
| 2012/0011570 A1 * | 1/2012 | Griffin | 726/4 |

OTHER PUBLICATIONS

Bulucea, Carmen Aurora, et al., "Real Time Medical Telemonitoring of Sustainable Health Care Measuring Devices," Proceedings of the 8th WSEAS International Conference on Artificial Intelligence, Knowledge Engineering and Data Bases, Cambridge, United Kingdom, Feb. 21-23, 2009, pp. 202-207.

* cited by examiner

*Primary Examiner* — Tai T Nguyen
(74) *Attorney, Agent, or Firm* — Harness, Dickey & Pierce, P.L.C.

(57) ABSTRACT

The system includes a computer-readable memory having a data structure configured to store information about a time-based event for a patient having reduced cognitive abilities, and optionally also electronic data reflecting the patient's cognitive ability. A networked computer system coupled to the computer-readable memory provides an information communicating interface to the patient. The computer system is programmed to monitor context information relevant to the patient and to dynamically adjust the presentation of the stored information based on the context, and optionally also based upon the patient's cognitive ability.

37 Claims, 26 Drawing Sheets

Mary
Today is
Monday

October 10, 2011 8:50 AM
Morning

320

☑

Morning Pills

Lunch with Joe
Meet in Lobby
In about 3 Hours

Noon
12:00

Alice will Visit
Tomorrow

Afternoon
3:00PM

Figure 3

| Event Title & Notes | After Event Starts | Event Start | Event End | Starts Showing | Entered By & Edit Options |
|---|---|---|---|---|---|
| Morning Pills | Did you take Pills? | Mon - Dec 12, 2011<br>9:00 am<br>'Please take your pills'<br>30 min. before | 1 Hr. 57 Min.<br>10:57 am<br>Repeat Daily | 30 Min. before event<br>Will show OK Button<br>30 Min. before event<br>Alert Enabled | gary johnson |
| Dinner with Jerry | | Tue - Dec 13, 2011<br>6:00 pm<br>No Music | 2 Hrs<br>8:00 pm | Now Showing | Jerry Lowe<br>*Edit* ← 1310 |
| Your Birthday Soon | Happy Birthday | Wed - Dec 14, 2011<br>All Day<br>No Music | Repeat Yearly | Now Showing | gary johnson |
| Lunch with Joe<br>Meet in Lobby | | Fri - Dec 16, 2011<br>12:00 pm<br>Soft Piano<br>20 Min Before | 2 Hrs<br>2:00 pm | Dec 15, 2011<br>Day Before Event | gary johnson |
| Visit Alice<br>Joe will pick you up | At Alice's | Sat - Dec 17, 2011<br>11:30 am<br>Soft Piano<br>20 min. before | Tue - Dec 20, 2011<br>6:00 pm | Now Showing | gary johnson |
| Christmas is coming | Merry Christmas | Sun - Dec 25, 2011<br>All Day<br>No Music | Repeat Yearly | Dec 21, 2011<br>4 Days Before Event | Valley Home<br>Sacramento<br>Group ← 1320 |

1300 points to top-right header row.

Figure 13

Manage Frame

First Name*: Mary
Last Name*: Smith
Frame's Time Zone*: Pacific
City and/or Room that Frame is in*: 300
☑ Allow Group Events Submit 1700
1710
1720
1730

Figure 17

CONTEXT DEPENDENT APPLICATION/EVENT ACTIVATION FOR PEOPLE WITH VARIOUS COGNITIVE ABILITY LEVELS

CROSS-REFERENCE TO RELATED APPLICATIONS

This application claims the benefit of U.S. Provisional Application No. 61/631,500, filed on Jan. 6, 2012. The entire disclosure of the aforementioned provisional application is incorporated herein by reference.

TECHNICAL FIELD

This disclosure relates a computer-implemented system for assisting persons of reduced cognitive ability to manage upcoming events.

BACKGROUND

This section provides background information related to the present disclosure which is not necessarily prior art.

People with early to moderate Alzheimer's or Dementia suffer from both memory loss and the inability to operate complex devices. These people are often anxious about missing events or activities, or forgetting other time-based issues. Consequently, these people often write copious notes to themselves. The accumulation of notes results in another form of confusion because they forget which notes matter and when they matter.

Notes placed on calendars are not always effective because the current date and/or time are not always known. In fact, keeping track of today's date, which day of the week it is, or even what part of the day it is (e.g. morning vs. evening) can be challenging.

If the person with Alzheimer's does remember that an important event is coming up, but this event is still many days or weeks away, anxiety can set in because they remember the event, but not when it is. Or, they can mistakenly think the event is happening tomorrow, even it is not happening for several weeks away. Consequently, people get told the wrong information by this person and/or repeated phone calls are made by this person to friends or family asking about details of the event.

If the person with Alzheimer's needs to remember a periodic activity, such as taking pills at certain times of the day, the first challenge is to remember to take the pills. The second challenge is to remember that they took the pills after they have already done so. The third challenge is giving a remote friend or family member some indication that the pills were taken so that a reminder phone call could be made if not.

Friends and family that wish to remind this person about an event may try to add their own notes, if they happen to be visiting. But, again, these notes can add to the pile of other notes that often get ignored or forgotten. Further, if someone takes this person on a short trip, other people may not know about this trip and consequently wonder if this person is OK when the phone is not answered.

If the person with Alzheimer's is in an assisted living home, staff can put a reminder note in an obvious place on the day of an event; but, placing these notes requires labor and the note is still often ignored when it comes time for the event to start. Consequently, staff may have to visit the person again to remind them when it is time.

Thus in an age of accessibility, the idea of being able to have one's medical records, doctor's contact information and even one's calendar schedule at the click of a button seems commonplace. However, for the over five million people who suffer from mental diseases such as Alzheimer and dementia, such use of these commonplace conveniences is beyond reach. Such persons are incapable of utilizing the new technology and applications due to age or mental diseases such as Alzheimer's disease and dementia. Individuals with impaired cognitive abilities have difficulty focusing and are easily confused, making it a challenge to interact with displays, computers, remote controls and many other daily objects/devices. Further, cognitively impaired individuals require the constant assistance of third parties (e.g. family members, friends, and other such caregivers) to perform simple day to day tasks.

Individuals with impaired cognitive abilities, herein referred to as patients, are not completely incapable of independent actions. Many are capable of getting dressed and feeding themselves, yet it may be the simple action of remembering to perform such an action that prevents them from living without the assistance of a third party.

Current market technologies include products such as portable data storage devices for medical records, emergency notification devices, portable medical monitoring system, daily calendar alerts, etc. However, all of these devices require the continuous action of a third party and/or are limited in their usage due to the patient's cognitive ability.

While third parties can assist people with impaired cognitive abilities to perform simple tasks (such as remembering events), there is a need to develop automatic solutions which assist people with varying levels of impaired cognitive abilities to perform and enjoy a variety of tasks and events in a natural and non-intrusive manner.

SUMMARY

This section provides a general summary of the disclosure, and is not a comprehensive disclosure of its full scope or all of its features.

The disclosed computer-implemented system assists persons of reduced cognitive ability. It can dynamically offload mental tasks of the patient to a computer system based on the patient's cognitive ability. In addition, it provides an interface that dynamically customizes the manner of interaction with the patient based on the patient's cognitive ability. In some instances the patient's reduced cognitive ability may be due to a diagnosed medical condition, such as Alzheimer's disease or dementia. In other instances the reduced cognitive ability may be due to other factors such as aging, stress and anxiety or other factors. The disclosed system is capable of assisting patients in all of these situations, and is thus not limited to diagnosed medical conditions such as Alzheimer's disease or dementia.

In one aspect, the disclosed computer-implemented system employs a memory having a data structure configured to store electronic data indicative of a patient's cognitive ability. The computer system is programmed to dynamically present information based on the patient's cognitive ability, as ascertained by accessing the data structure.

In another aspect, the computer system is programmed to acquire and store context information relevant to the patient.

The computer-implemented system uses patient's cognitive ability, and/or context information to customize how interaction with the patient, and also with third parties, such as the patient's caregiver is performed. As used herein, the term "caregiver" is intended to refer to any person who provides assistance to the patient, including family members, doctors, professional nursing home staff, and the like.

The computer-implemented system, based on the patient's cognitive ability and/or context information, dynamically renders assistive information to the patient, dynamically and automatically launches computer applications to assist the patient without the necessity of the patient's mindful interaction. The system dynamically adapts and customizes the presentation of information to the patient by adapting the content and complexity of messages presented, by adapting the modality of multi-modal devices used by the patient, including providing audible and visual information to the patient based on cognitive ability and/or context. The audible information may include speech, which the system is able to dynamically adapt to suit the abilities and needs of the patient, as by adapting the vocabulary, speaking speed, grammar complexity and length of messages based on cognitive ability and/or context.

In another aspect the system employs a computer-implemented data store configured to store plural items of information about a time-based event for a patient having reduced cognitive abilities. A networked computer system coupled to said data store provides a first information communicating interface to the patient and a second information communicating interface to a caregiver associated with the patient.

The data store has a data structure in which to store electronic data indicative of the patient's cognitive ability. The networked computer system is programmed to receive, through the second interface, plural items of information about a specific time-based event and is further programmed to store the received plural items of information as a record in said data store associated with said specific time-based event.

The networked computer system is further programmed to supply information to the patient through the first interface in a fashion such that the stored plural items of information associated with the even are used to construct a dynamic message communicated to the patient in increasing levels of detail as the time of the event draws nearer.

In addition, the networked computer system is further programmed to access the data structure storing said electronic data indicative of the patient's cognitive ability so as to control the manner in which the dynamic message is delivered to the patent based on the accessed electronic data.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 3 shows an example messaging seen on display device after a reminder was acknowledged

FIG. 13 illustrates an example user interface as seen by a regular user for reviewing all active reminders and messages for a particular display device.

FIG. 17 illustrates an example user interface for managing parameters for a particular display device.

Corresponding reference numerals indicate corresponding parts throughout the several views of the drawings.

DETAILED DESCRIPTION

Overview

Figure 1:
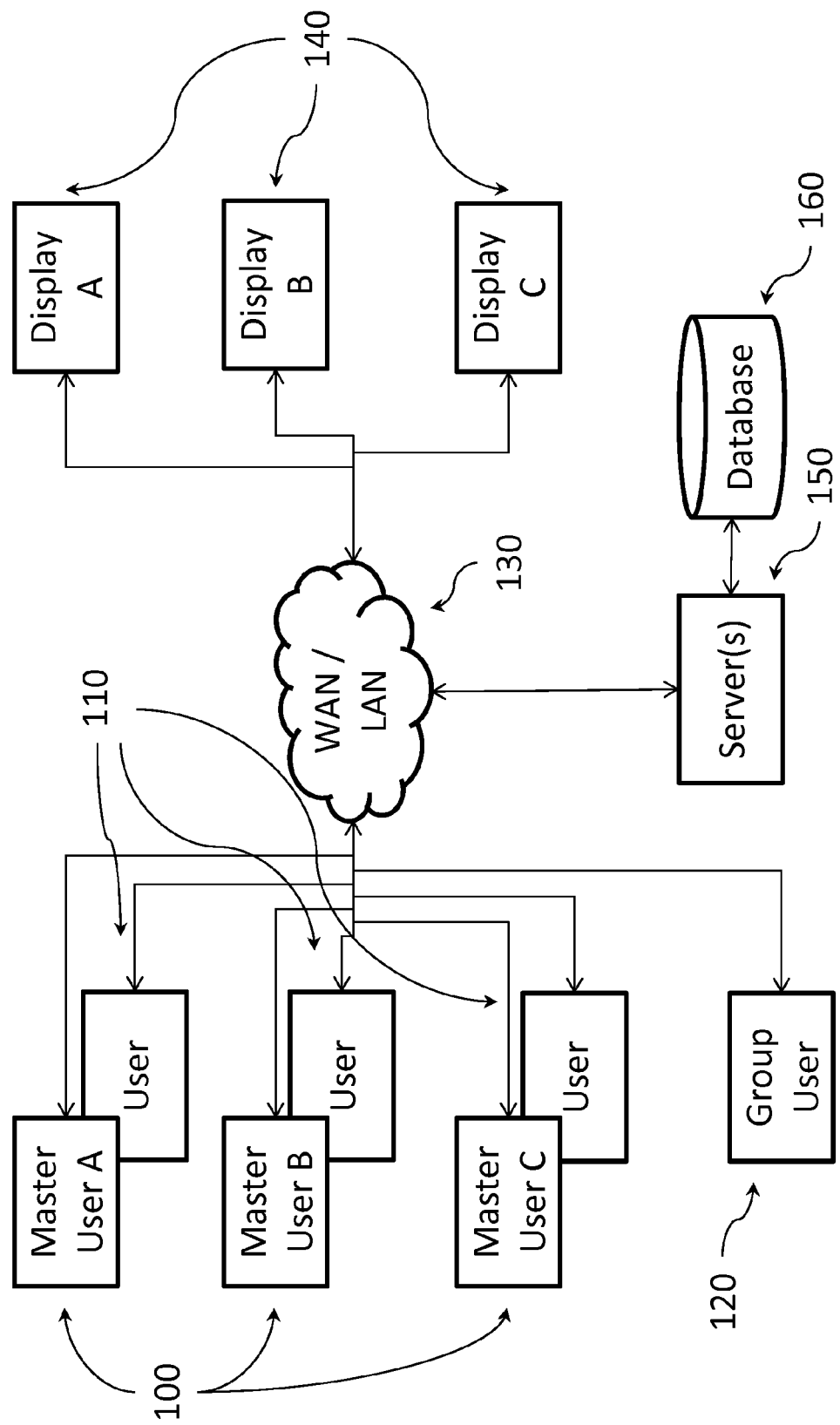
FIG. 1 shows a general system architecture showing users, display devices, server-based system, and network.

The disclosed system lets people (e.g. friends, family, administrators) in a remote or local location create reminder messages that will show at the appropriate times and with appropriate messaging on a relatively simple display device. This display device need not have any controls that the viewer interacts with, so a person with Alzheimer's does not need to learn how to operate it. The only interaction that this display device needs happens during a one-time initial setup step, and optional reminder acknowledgements that require only the press of one button.

The system works via a network, such as the Internet and/or local area network (LAN). People (friends, family, administrators) interface to the system via any modern browser. The system, in turn, interacts with the display device via the network.

The system accommodates multiple display devices and multiple accounts. More than one person can be given the ability to create a reminder message. A master account(s) is also given the ability to edit messages from other accounts, as well as other privileges. For situations, such as an assisted living home, a group administrator account can send messages to groups of display devices, or to just one display device. However, accounts that are associated directly with a particular display device can hide such group messages if needed.

Account holders associated with a particular display device can see each other's reminders, including group messages, so that friends and family can be informed about the planned or current activities of the person for which the reminders are intended. However, group account holders can only see their own group messages, unless permission is granted otherwise, to preserve privacy.

Messaging can be set up in advance, and made to appear at the appropriate time relative to the event they refer to. The content and level of detail of the messaging, including audio, changes according to how close it is to the event in question. Once the event starts, messaging continues until the event is finished, and the content of this messaging changes according to when it is relative to the end of the event.

Reminders can be programmed to automatically repeat at specified intervals, from daily to yearly, to accommodate a variety of situations and events.

Reminders can optionally require that an acknowledgement by the viewer take place. Multiple acknowledgement requests can be active at one time. If such a reminder is not acknowledged, remote users (friends, family, and administrators) can check the status and/or receive an alert via a short message service or email.

Preset reminders exist to help save typing. Account holders can use system defined preset messages or create their own for future use. Preset messages can be customized by the account user.

Messages can also be "instant messages" that are not tied to any particular event. Such instant messages appear relatively quickly and do not require any action by the viewer to see.

To avoid potential failure situations, such as equipment failure, loss of power or communications, the system can monitor the health each display device and alert the appropriate account holders and/or administrators of such a failure.

In one aspect the system focuses on providing hybrid care assistance dependent on the cognitive abilities of a patient, ranging from full third party control to shared control to an independently functioning patient, in an automatic and natural manner. Third party control of the system can be local or remote. Further, the system itself will adapt the level of interaction provided to the patient based on further improvement or decline in cognitive ability.

Thus, the system works to automatically and naturally adapt the triggering of events (e.g. launching applications/events on a display) based on the following core functionalities:

A. Arm/set the event/App by a third party (e.g. family member)
B. Estimation of an event context. The context can take several forms (medical, situational, etc.) depending on the event to be triggered
C. Launch of the event based on matching the context with present situation and the person cognitive ability.

In addition to the above core functionalities, the system also offers an number of additional advantages, including the following:

An application can be triggered automatically in a non-intrusive way (e.g. audio message when the patient is not sleeping)
The launch and the interaction with the application can be customized to the patient cognitive ability.
The patient can enjoy a number of services (e.g. see family pictures, video conference or reminders) without having to know how to launch the application/event.
Personal preferences of the patient can be taken into account to customize the system's services.
The solution includes implicit interaction (from the patient point of view) with explicit interaction (from the third party who arm the event/application point of view)
Our solution is about when to launch an application/event, and how to launch an application/event.

DETAILED DESCRIPTION

Example embodiments will now be described more fully with reference to the accompanying drawings.

FIG. 1 illustrates the general system architecture, showing a set of different types of remote users, a server system and a set of display devices (or simply "display" or "displays" in subsequent descriptions). Each User 100, 110 interacts with the system via the network 130, which can be a combination of wide area (such as the Internet) or local area networks. Each user is associated with a particular display 140. In the illustration, Master User A 100 and a related normal User 110 interact with Display A. In turn, there is a separate set of users associated with display B, etc.

User accounts center around the display. There is at least one Master User 100 associated with each display. The Master User has ultimate control over how the display looks. The Master User can do the following:

Create new event reminders and messages.
Edit event reminders and messages that they created or those created by any other Master or Normal user that belongs to the managed display.
Create new Master or Normal users for their display.
Controls whether or not Group events are enabled on their display (see Group users).
Hide or Show a specific Group event reminder that was sent to their display. Hiding a Group event reminder might be necessary if this event is in conflict with another event that the Master (or Normal) user has planned.
See event reminders and messages that anyone has created for their display.
Create and edit preset event reminders that others can also use.
Change the display's details, such as names, location and time zone.
Change their own user details, such as names, username, email address and password.

Normal or regular Users 110 can place messages on this display, but have fewer privileges:

Edit event reminders and messages that they created.

Hide or Show a specific Group event reminder that was sent to the display.

See event reminders and messages that anyone has created for the display.

Create and edit preset event reminders that others can also use.

Change their own user details, such as names, username, email address and password.

Group users 120 can be associated with more than one display. FIG. 1 only shows one group user to illustrate a situation where there are three displays (A, B, C) at a particular facility that this group user has access to. Master Users can do the following:

Invite a Master user to join this Group by sending them an email invitation. To send such an invitation, the Group user will need to ask for the Master user's 'username'. The Master user that receives the email invitation to join the Group must then click on a link to accept the invitation. The Master User still reserves the right to disable any or all Group events from showing on their display.

Create and edit Group event reminders and instant messages that go to all displays enabled to accept group events from this Group user.

Specify that an event reminder or instant message go to just one display (instead of all displays).

Group users cannot see the event reminders and messages that have been created by Master and Normal users for any particular display, unless permission is given to expose a particular item.

Change their own user details, such as names, username, email address and password.

The Server 150 manages the system, including the access to the system by each of the users and the updating of each of the displays. Again, FIG. 1 only shows a subset of what is possible because one server 150 can manage a number of set of users and displays scattered around the world. Databases 160 store the all of the information on all users, displays and messages. Sensitive information, such as passwords and email addresses are kept encrypted.

In a typical operation a user interacts via a web browser or dedicated application with the system to create a reminder. This reminder is stored in the database and the server then determines which reminders should go to each particular display at the appropriate times. Users can view the status of all reminders and messages, including making edits and hiding messages as appropriate.

The displays merely display the messages that they are sent. Optionally, they can do a small amount management of these messages to minimize the amount of communications needed during operation. Optionally, these displays may provide a simple way (e.g. touch the display, verbally, etc.) for a viewer to respond to a message, if requested, and this response is sent back to the server.

Figure 2:
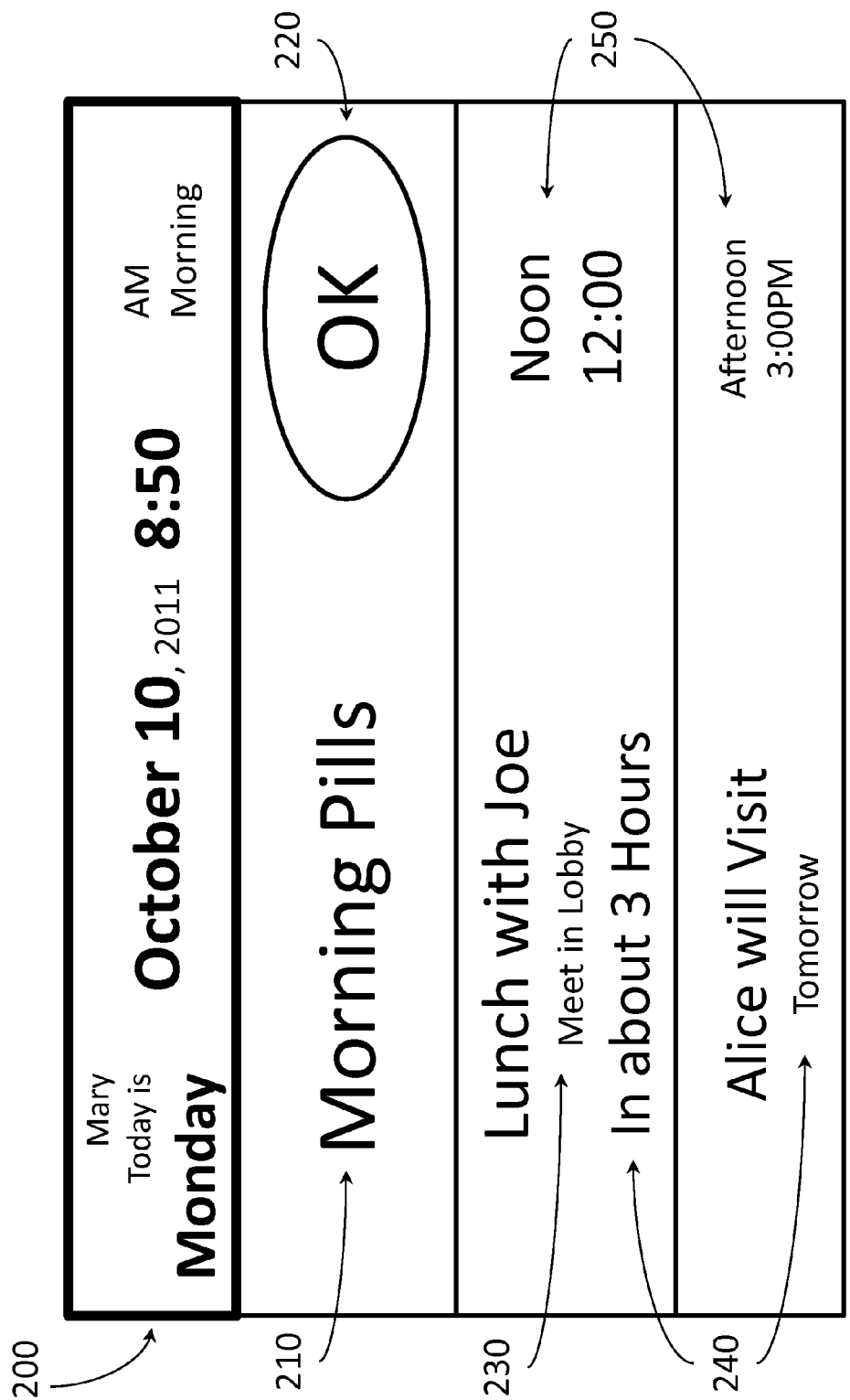
FIG. 2 shows an example messaging seen on a display device.

FIG. 2 illustrates a typical type set of messages that might be seen on a display. Because complex messages and even graphics can lead to confusion if a person has Alzheimer's, messaging must be kept simple, direct, and appropriate to the situation.

The top of the display 200 simply shows the current date and time. The part of the day, such as "Morning" or "Evening" is also shown. Time and date are automatically obtained from the network. Since the display can be in one time zone while a user is in another time zone, the display's time zone is determined by a selection 1710 made by the display's master user.

In the sample display, event or reminder "titles" 210 are shown on the left because the illustration assumes people tend to read from left to right. Of course, different cultures can work differently, and so adjustments to how the display if arranged can be adopted to different countries.

Message titles are kept deliberately short by limiting their length in the input menu 1100.

The size and font color used to display the message title (and other parts of the messaging) change according to how close it is to the event in question. The closer it is to the event's start (and end if the event is of any length) the larger the font and more urgent the color.

Since message titles might be too short from some occasions, a second line 210 is allowed for putting additional messages or instructions. This second line is optional and it can be made to not appear until the time gets closer to the event. This delayed showing of the second line follows the assumption that showing too much information too early would only confuse the reader.

Additional messaging 240, 250 is added to reminders to give clues on when an event is to take place. The wording of the supplemental timing messages is designed in a simple conversational style. It would be too confusing to the reader to say that an event is supposed to start at "11:30 AM, Apr. 10, 2011" if it something like "In about 2 Hours" can communicate the same thing. The algorithms for how such timing messaging works can be fairly involved and must be tailored to the cultural and language norms of the viewer. As always, messaging must be kept to a minimum; but, it can also be a problem if too little information is given.

Figure 22:
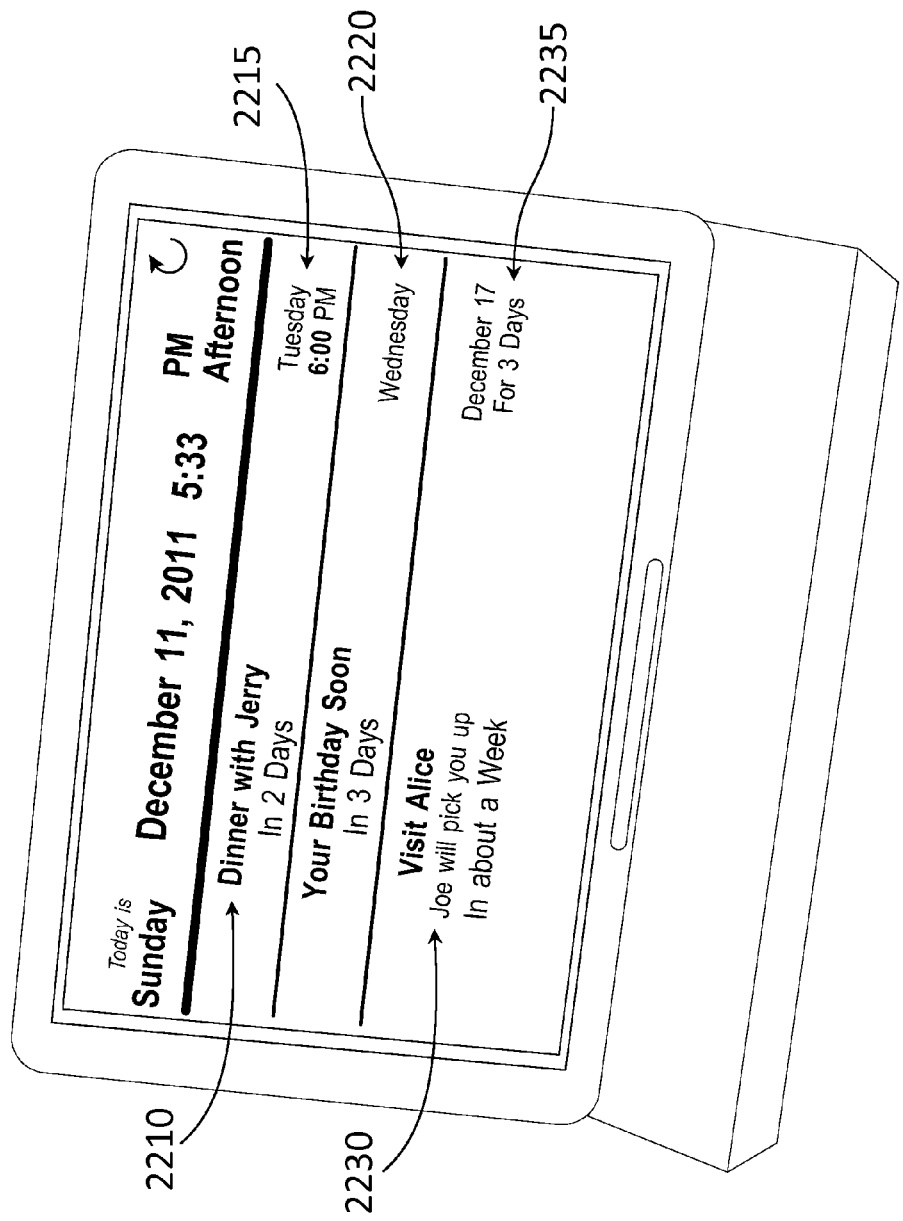
FIG. 22 depicts an example display device showing a few example reminder messages.

FIG. 22 shows more sample messaging on a working display.

The sample message "Morning Pills" is asking for a response—in this case the pressing of the "OK button" 220. Instructions on how to respond can be given verbally or by other means. In this illustration, the OK button is simply a graphic on the display, and the system senses the pressing of this button by using a touch sensitive display 1015 system. The status of the response can be monitored, as is explained later.

FIG. 3 shows a similar sample display to FIG. 1, but with one difference—the OK button has been replaced with a checked box icon 320. This icon, or a similar type indicator, tells the viewer that the message was acted on. Sometimes people will forget that they already acted on something that they regularly do, such as taking pills. The checked box icon serves as another form of reminder.

Figure 4:
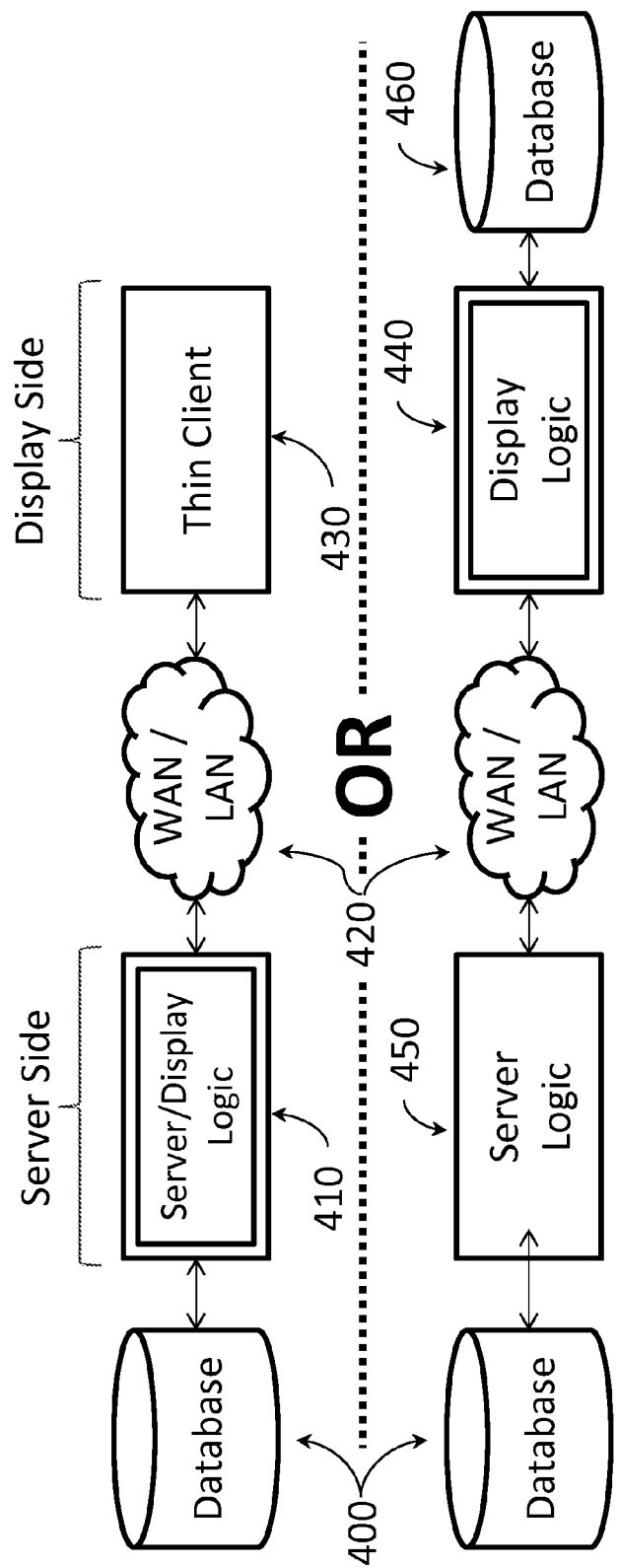
FIG. 4 shows examples of alternative approaches for where to place system logic within the overall system

FIG. 4 shows a couple of ways to distribute the system's logic.

The top version places almost all logic in the server side 400, 410 and the display 430 is not much more than a thin client, such as a browser connected to the Internet 420. Such an arrangement means that off-the-shelf products, such as modern tablet computers can be used for the display.

In this arrangement, the tablet computer is basically used as a browser display. HTML and PHP commands in various web pages determine what to display and when to display it.

Refreshing of the display just after the top of each minute, or at other selected times, is programmed into the webpage by reading the network time and calculating the time for the next auto-redirect command (header('Location: page_url.php')). Upon each refresh the display can update the displayed time of day, retrieve new messages and update the wording and fonts of currently active reminder messages. Audio can be played, if required, via commands found in HTML5, or alternatives.

The bottom version places some of the messaging logic into the client side 440. Information on future events can be stored locally in the display's local database 460. Algorithms that have been placed into the display's system can then determine what to display at any given time without having to communicate with the server's system. The display will still need to periodically communicate with the server to get message updates, but such communication can be less frequent. Much of the system's logic, particularly for Master, Regular and Group interfacing, account management and general system management, etc. still resides in the server 450.

Implementation can be done a number of ways. In one version, software code could effectively be downloaded into the display's browser using a language such as AJAX.

In another version, the display could contain a software application that stays resident in nonvolatile memory, if present. This software can be made to automatically execute when the display is first turned on. This means that power and communication interruptions can be automatically addressed.

Figure 5:
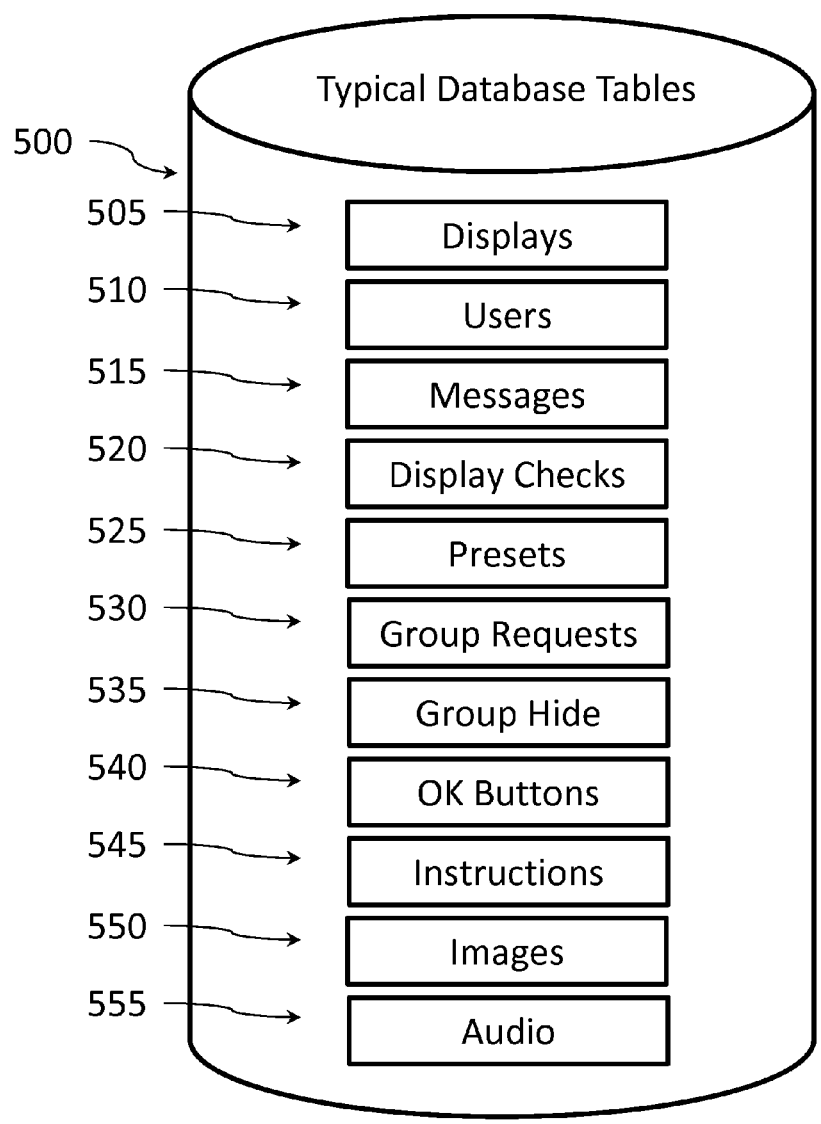
FIG. 5 illustrates exemplary database elements used by the system FIG. 6 provides an example of a simplified flow of logic for the display device

FIG. 5 shows categories of typical database 500 tables used in the system. During operation the algorithms stored in the server access the following database tables to determine how to handle each display, user and situation.

A table for Displays 505 contains information about each individual display, such as the names associated with the display and time zone. The table for Users 510 contains information on each user, including their names, contact information, passwords, and type of user account. Users found in this table are associated with a display or set of displays (if this is a group user). The Messages table 515 holds all of the messages, including information on how and when each individual message should be displayed, who created the message and type of message. These three tables comprise the core of the database used by the system.

In addition to the core tables, there are a number of important supplemental tables. The Display Checks table 520 is used to store the health of each display. The Presets table stores predefined messages that can be used to save some typing. These preset messages contain most of the same information as regular messages stored in the Messages table. The Group Requests table is used to store requests that a Group User has made to Master Users to join a group. The Group Hide table is used to store information that determines if a particular Group message should be displayed on a particular display, or not. The OK Buttons table stores the status of responses for each message that requires such a response. The Instructions table is used to store localized (different languages) instructions and wording for the user interface. The Images table is used to store images that can be associated with particular messages. The Audio table is used to store audio files in appropriate formats that can be associated with particular messages or situations.

Figure 6:
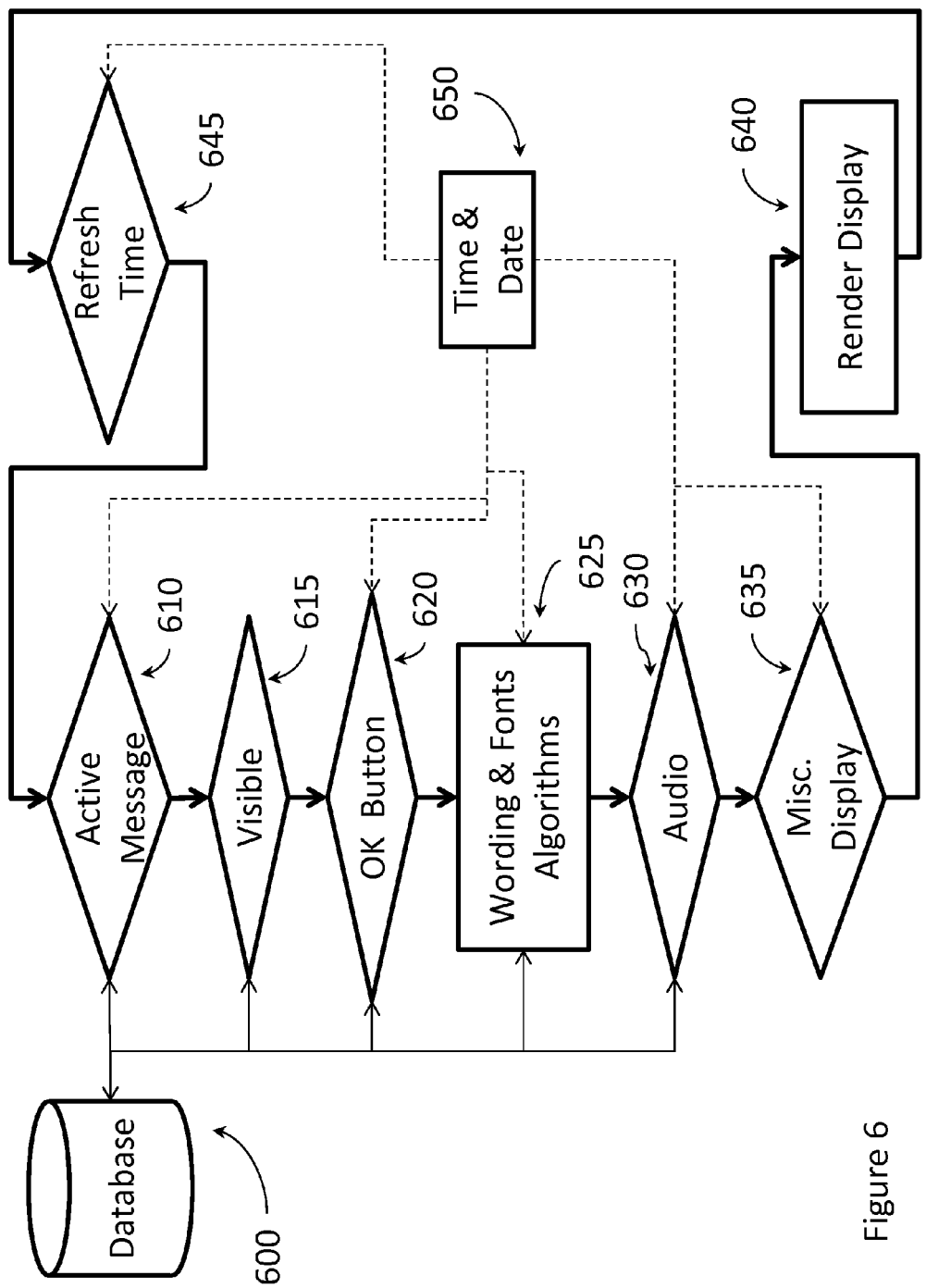

FIG. 6 begins to show how the algorithms and database tables work together to manage all of the displays.

At periodic times the database 600 is looked at to see which messages are currently active 610. A message is active if the entry in the Messages table indicates that a message should be displayed based on the current time zone, date and time 650.

Next, if a particular message comes from a Group User, the Group Hide table is accessed 615 to determine if this message should be displayed on this particular display.

Next, the OK Button table is accessed 620 to determine if a response is required at this particular time or not. A message can be displayed without requiring a response until a predetermined time before the event is to start. Thus, for example, a viewer can see that an event is about to come up, but a response from the viewer is not asked for until the event is just about to happen.

Next, based on parameters stored in the Messages and other tables, the exact wording and choice of fonts is compiled 625. How messaging is tailored to meet each situation is perhaps just as much an art as a science, but the important element of this disclosure is that such tailoring is integral to the system.

Next, if there is any audio associated with the message or situation, the Audio table is accessed and compiled 630 into the message as appropriate. As with the wording and fonts chosen earlier in the previous step, audio can be tailored, too.

Similarly, if there are any graphics or images associated with the message, these are also integrated in 635. Again, tailoring to fit the situation can be done.

Finally, the complete compiled message is rendered on the display 640. This includes any text, audio and/or images that were determined to be part of the message in earlier steps. The display and message is then refreshed as necessary based on the refresh timer.

Figure 7:
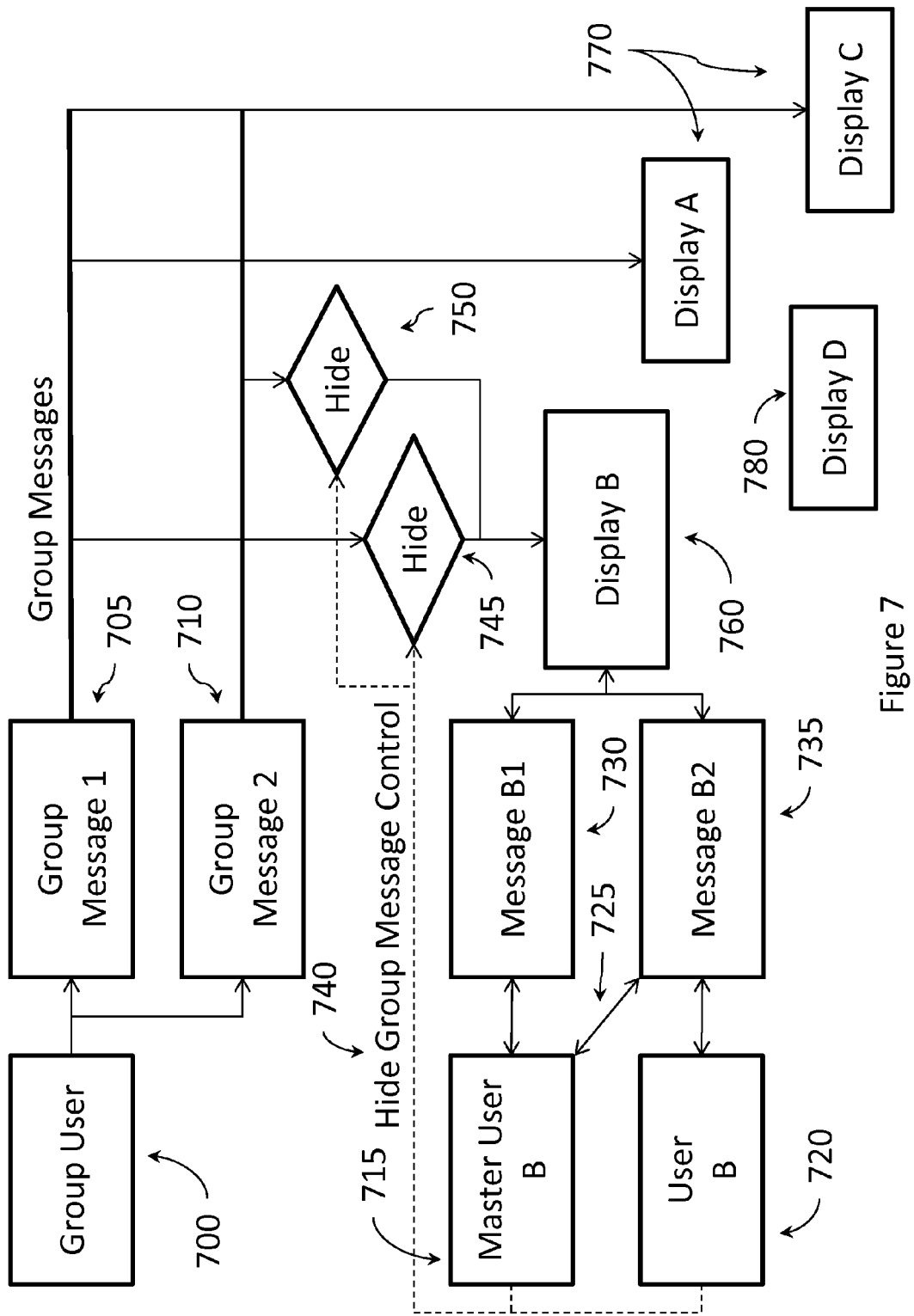
FIG. 7 shows the relationship of group messages and different types of users for a particular display device

FIG. 7 shows a part of the relationship between a Group User 700, Master User B 715 and regular User B 720 when placing messages on a particular display.

The simplest situation is when a Master User wishes to place a Message B1 730 onto the Display B 760. Since Display B is managed by this user, the message is allowed. Other displays in the network, such as Display A, Display C 770 and Display D 780, ignore Message B1. Similarly, User B can place a Message B2 735 onto the same Display B because this user has been authorized by Master User B to do so.

Master User B also has the ability to edit or delete Message B2 that was created by regular User B. But, while regular User B can also edit Message B2, this user cannot edit Message B1 created by Master User B.

Both Master User B and regular User B can see all off the messages that are directed to Display B, whether or not they are currently showing on this display.

The Group User in this diagram is shown as creating two Group Messages 705, 710. These group messages potentially go to all displays 760, 770 that belong to this group, but not displays 780 that are not part of this group, even if such displays are on the same network.

When a Group Message is directed at any display, the Master and regular Users associated with that display also see this message. If either the Master or regular User decides that a Group Message conflicts with an event that they are planning, these users have the ability to hide this Group Message. Each individual Group Message can be allowed to show or be hidden, so Group Message 1 705 can be hidden 745 independently from Group Message 2 710 being hidden 750. Decisions by this Master User B and regular User B do not affect what is shown or not on other Displays 770, 780.

Figure 8:
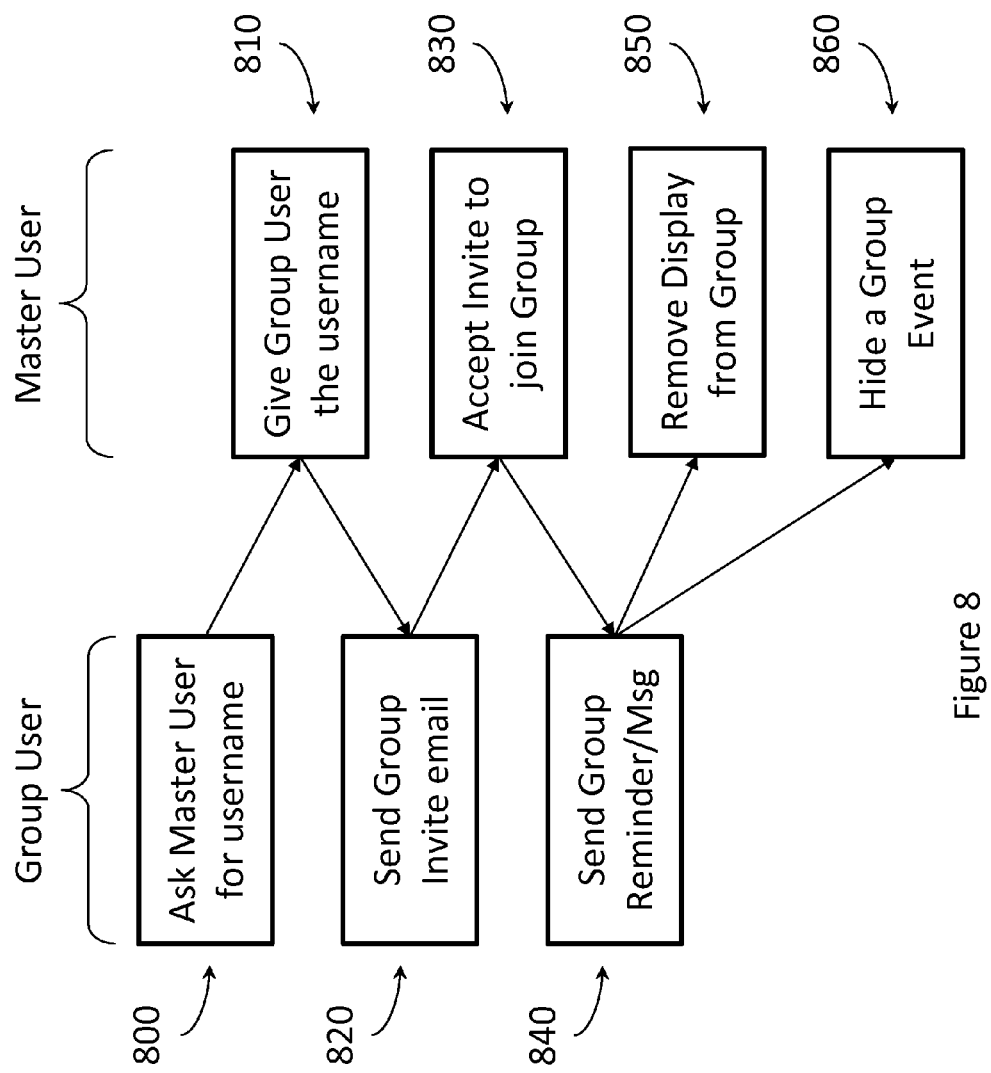
FIG. 8 shows an example process for setting up a relationship between group and master users for a display device

FIG. 8 shows the flow of activities that determine if a particular display is part of a particular group. Control of the display belongs to that display's Master User, so the Group User must first ask for the Master User's username 800. If the Master User agrees 810, the Group User can then send that Master User an invitation via email to join the group 820. This email contains a special link with an encrypted key that, when clicked, takes the Master User to a web page that displays the group the display just joined 830. From this point the Group User's Group Messages will be seen on the display in question 840, unless the Master User decides to remove this display from the group 850 or hide that particular Group Message 860. Normal Users can also hide individual Group Messages (similar to step 860), but cannot remove the display from the Group.

Figure 9:
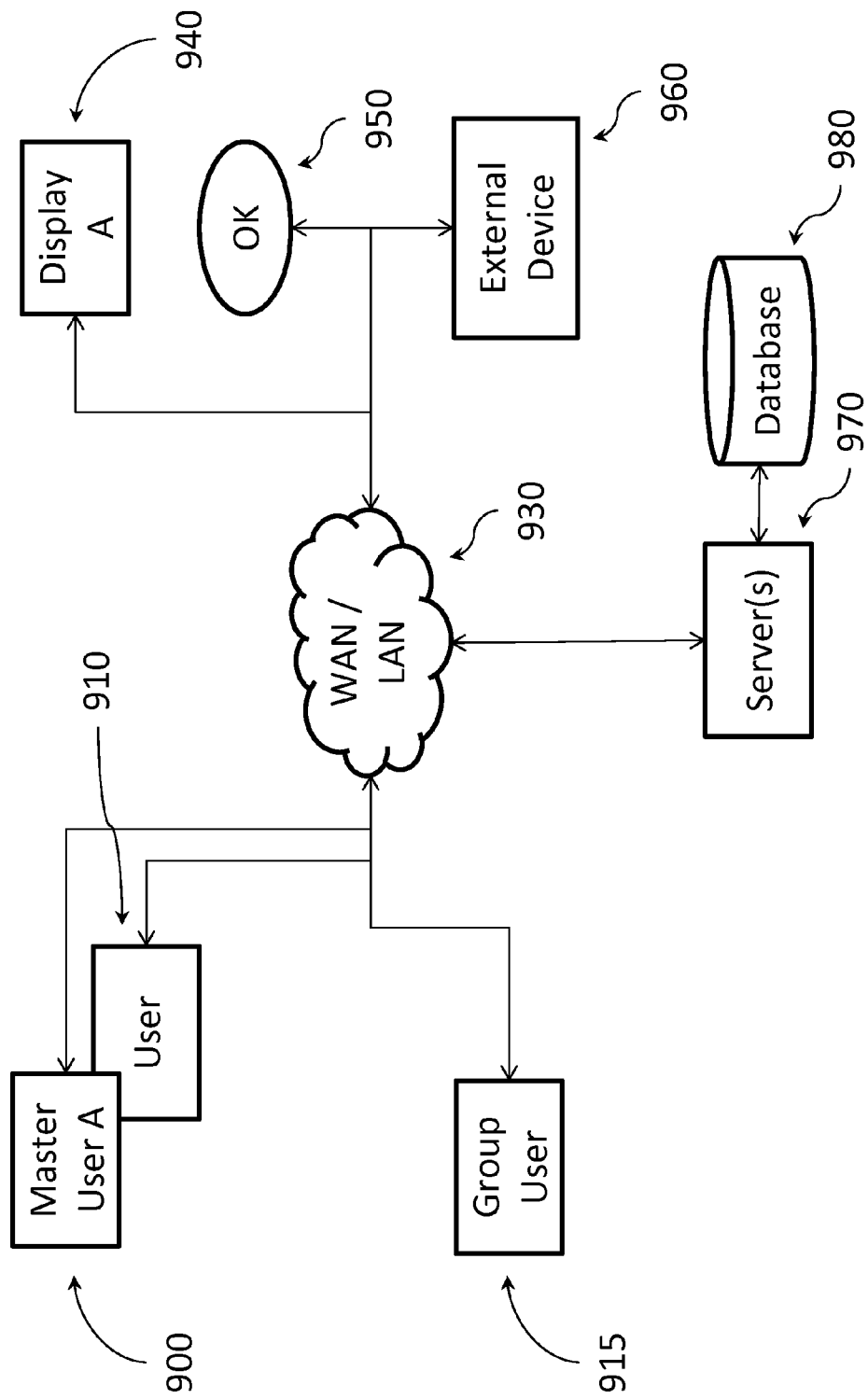
FIG. 9 illustrates a subset of system for illustrating reminder acknowledgement

FIG. 9 shows a variation of FIG. 1, and is used to illustrate how the OK button or acknowledgement system works. First, a reminder message is created by the Master 900, regular 910 or Group User 915 that specifies the need for an acknowledgement by the display's viewer. The message is saved in the database 980 and served up 970 to the display 940 at the appropriate time. Then, at the specified time, the OK button is displayed 950, along with any other verbal or visual prompts. Alternatively, an external device 960 can be activated to ask for some type of action. The requested acknowledgement is then made by the viewer and logged into the database 980. The various users can then see via a web page if the acknowledgement was made. Alternatively, the server can send a short message (SMS), email or even make a phone call.

Figure 10:
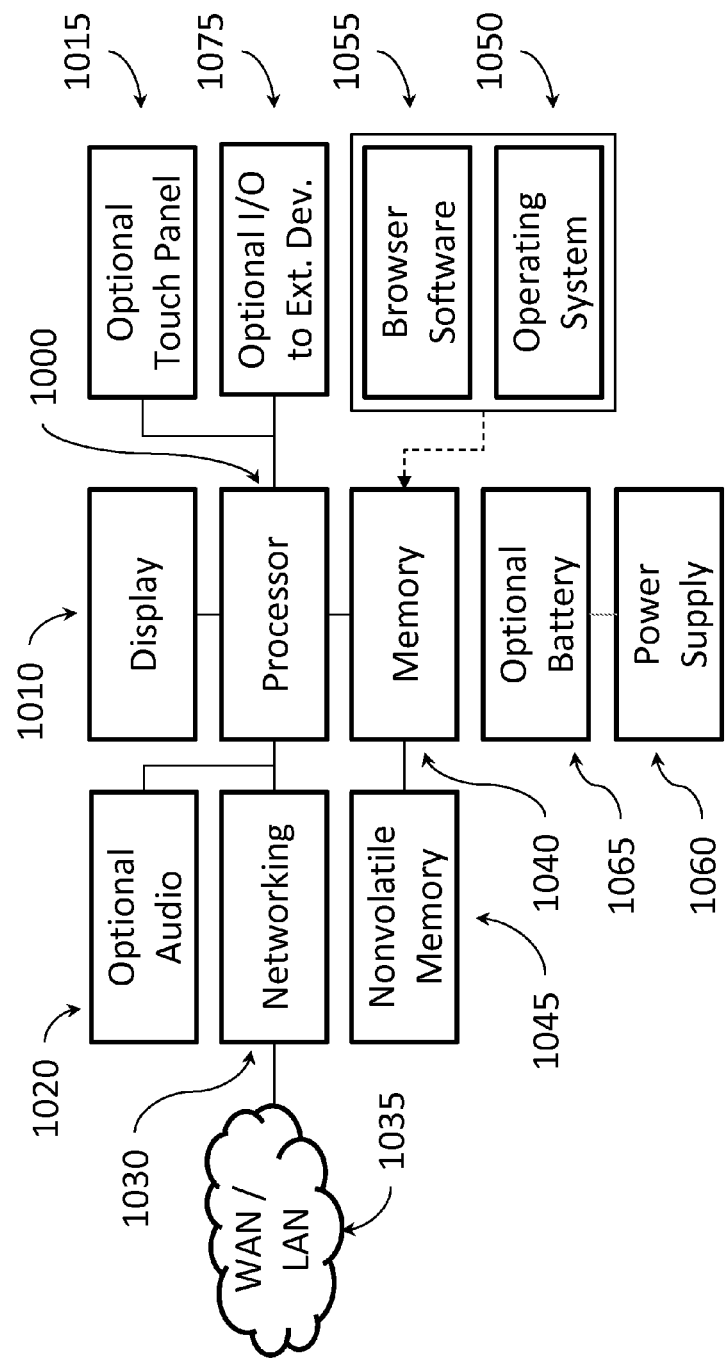
FIG. 10 shows an exemplary hardware block diagram for a display device

FIG. 10 shows a typical hardware block diagram of a display. The display consists of a typical set of elements, including a processor(s) 1000, memory for instruction operation and variables 1040, nonvolatile memory 1045 for BIOS, operating system 1050 and applications 1055, power supply 1060 and optional battery 1065, display 1010 and optional touch panel system 1015, networking (wired and/or wireless) 1030 for connecting to the WAN/LAN 1035.

This display can be a stand-alone product or be part of another product. For example, this display can be integrated into a television. If so, the touch panel user interface might be replaced with a remote control arrangement. Since most all of the other elements are already part of today's televisions, these elements can be shared and leveraged.

Figure 11:
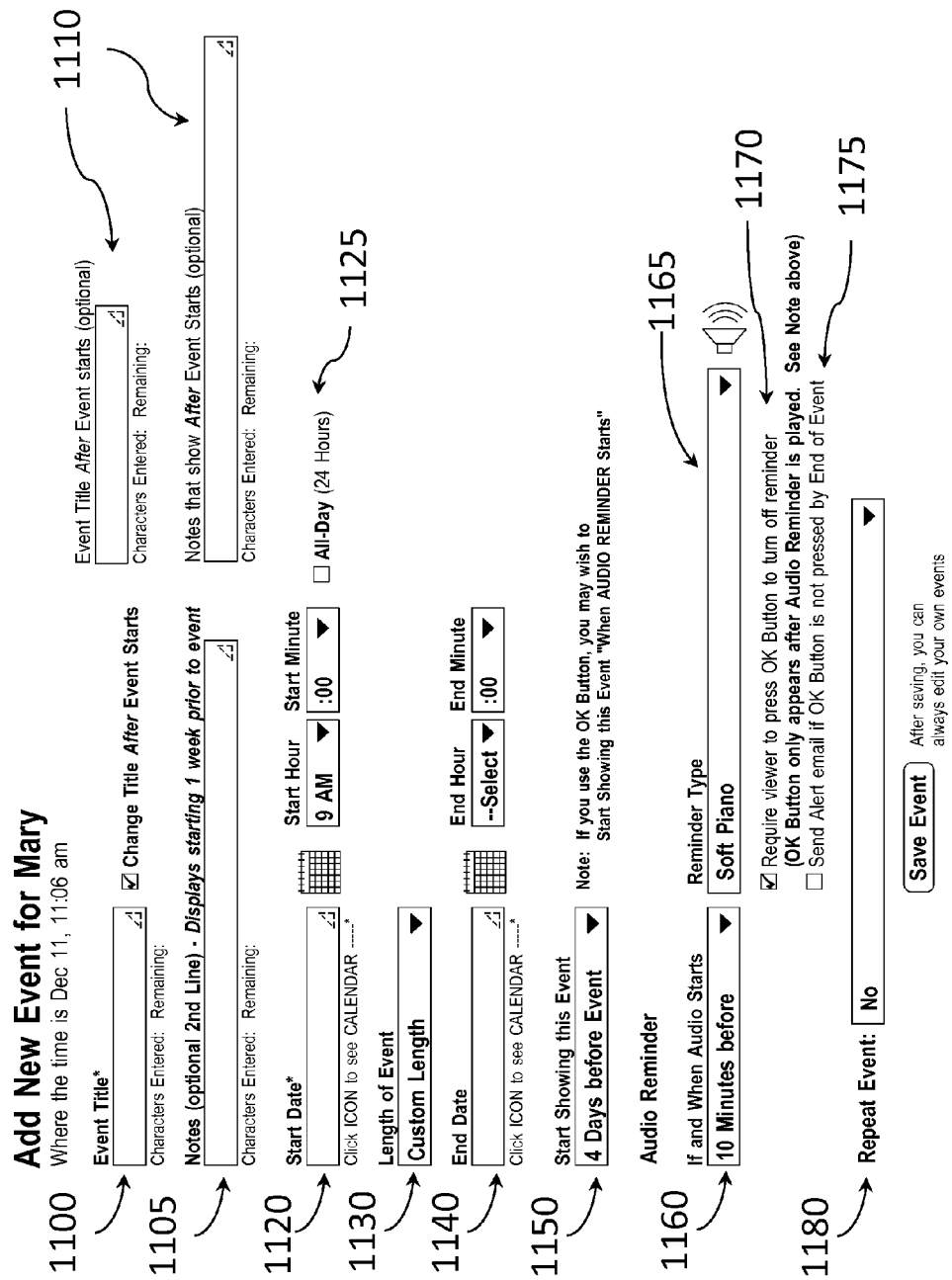
FIG. 11 illustrates an example user interface for creating and/or editing reminder messages

FIG. 11 shows an example user interface screenshot for entering or editing a reminder message. This can be part of a webpage or be part of an application.

It begins with a place for entering the message title or headline 1100. There is also a place to enter a second line of description 1105. While there can be even more lines, this illustration limits descriptions to just these two parts to keep the message to the viewer simple.

Sometimes it helps to change the message once the event starts. For example, a message can read "Your Birthday Soon" on days leading up to the birthday, but read "Happy Birthday" on the day of the birthday. To accommodate this option, a second set of message titles and notes are allowed for 1110.

Each reminder message is then given a start date and time 1120. Some types of events, such as holidays and birthdays are really about the day itself, so events can be designated as being "All-Day" 1125.

If the event is not an All-Day event, the next thing to specify is how long the event lasts 1130. If the event lasts less than a day the length of the event can be specified in minutes, hours, etc. If the event takes place over multiple days, the end of the event can be defined by specifying a specific date and time 1140.

Next, one can specify when to start showing the event on the display 1150. The timing of when to start showing the event is highly dependent on the type of event and preferences of the users and viewers, and is not tied to the length of the event.

Optionally, audio reminders can be played to draw attention to an event. One can specify when to start playing such audio messaging 1160 independently from when the event starts to show, except that audio messaging should not start until the message shows visually. The type of audio messaging can be chosen separately 1165.

If an acknowledgement of the reminder message is required, there is a checkbox that the user can check 1170. Further, if the user wishes to be alerted if acknowledgement is not given after a specified period of time (by the end of the event), another checkbox 1175 is provided for doing so.

If the event repeats in some predictable way, the system lets the user specify how this event should repeat 1180. A number of repeat options, from daily to yearly and several options in between can be provided. Unlike calendar systems used in PC, PDA and phone systems, only one occurrence of a repeating event is shown at a time to avoid confusion by the display's viewer.

Figure 12:
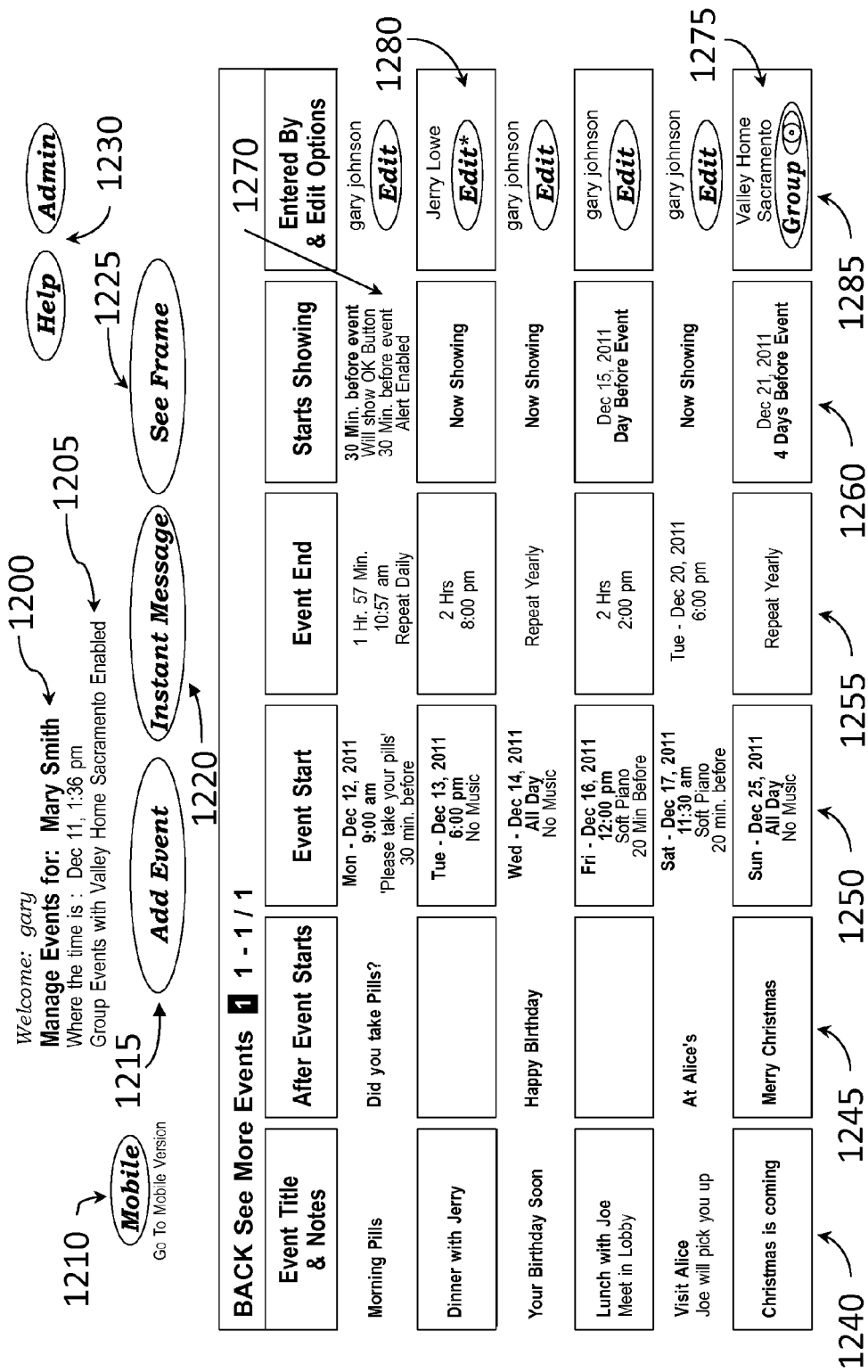
FIG. 12 illustrates an example user interface as seen by a master user for reviewing all active reminders and messages for a particular display device.

FIG. 12 shows a typical user interface that Master Users see for reviewing and managing all of the messages scheduled to show on the display. This can be found on a webpage or be part of an application.

The interface shows information about which display it is showing 1200, plus other supplemental information such as the time where the display sits, and if this display is enabled to accept Group Messages 1205.

There is a button for showing the information in a format that is friendlier for mobile devices 1210 (automatic switching to this mode is also possible). There are buttons for adding a new reminder message 1215 or instant message 1220. There is a button to see what the display itself looks like at the moment 1225. There are other buttons for displaying help and infrequently used administrative functions 1230.

The main table shows a summary of all of the active events currently lined up for this display. Table columns show titles and notes (1240, 1245), information on when events start and what the display should do at various times 1250, information on when events end and if or how they should repeat 1255, information on when events should start to show, or if they are currently showing on the display 1260. There is also information on if acknowledgements will be requested, or if an acknowledgement has been given or not, and if an alert should be issued if an acknowledgement is missed 1270. A final column shows who created the message 1275, and shows an edit button if the message is one that this user can edit 1280. Since FIG. 12 is for a Master User, this user has edit privileges for any message created by any other Master or regular User. The edit button can be made to look slightly different if the particular message was made by someone else 1280.

Not illustrated is flag that appears if two or more events overlap or conflict. Since different users can be placing event reminders onto the same display, one user could accidently create an event that conflicts with another, so it is important to give some indication of such a conflict.

For Group messages, instead of an edit button, there is a button that is used to hide or show that Group message. In this case, the button shows an open eye 1285 if the message is visible, but a closed eye if not. Specific implementations of this feature can be different according to user interface preferences.

FIG. 13 shows a similar illustration for managing reminder messages, only this one shows what it might look like for a normal User. Since a Normal user can only edit messages that they entered themselves, the edit button only shows on a subset of the listed messages 1300, and not for messages that others have created 1310. Since normal Users can hide and show Group Messages, they still see the button for doing so 1320.

Figure 14:
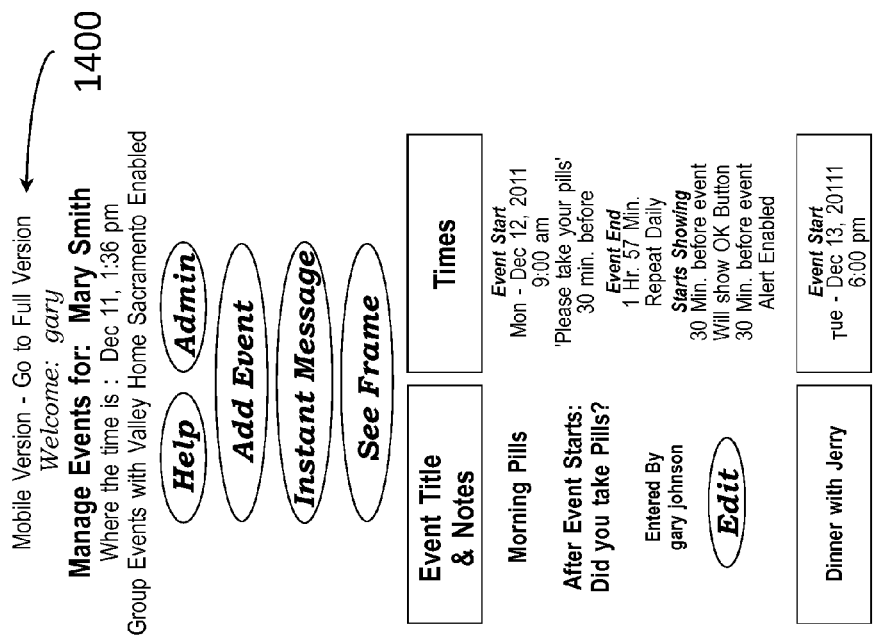
FIG. 14 illustrates an example of a similar user interface formatted for smart phones and other mobile devices.

FIG. 14 shows what these interfaces might look like for a mobile device. Only part of the overall interface is shown— the rest can be seen by scrolling or paging. There is also a way to get to the "full" interface 1400.

Figure 15:
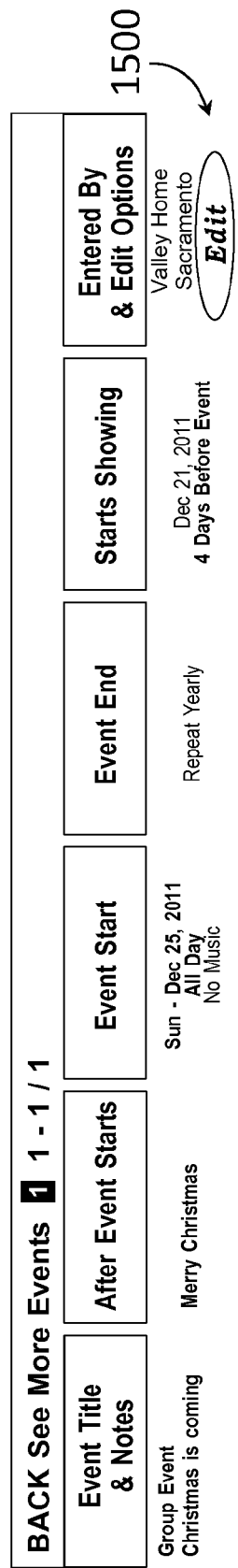
FIG. 15 illustrates an example user interface as seen by a group user for viewing group reminders and messages.

FIG. 15 shows what the interface might look like for a Group User. Since the example being used only had one Group Message in it, only one message 1500 is shown on this table. Unlike Master and normal Users, a Group User can edit a Group Message, so we also see an edit button.

Figure 16:
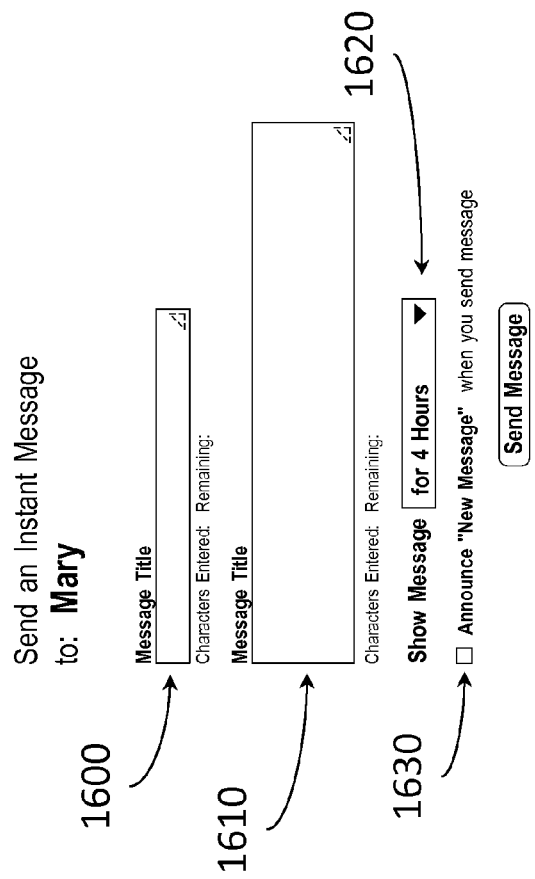
FIG. 16 illustrates an example user interface for creating or editing an instant message.

FIG. 16 shows a typical interface for sending an Instant Message to a display. A place for a message title 1600 and second line of details 1610 is given. A way to specify how long the message should be displayed is then provided 1620.

Unlike typical instant messages used on phones or PCs, the viewer of the type of display described in this disclosure is a more passive viewer. No action is required by the viewer to get the message onto the display, but at the same time, there is no guarantee that this person will ever notice the message. To draw attention to the message an audio notice can be specified 1630. Alternatively (not illustrated here) a message can be made to ask for an acknowledgement, similar to messages illustrated earlier.

FIG. 17 shows a part of the system's administration functions—in this case the management of the display (or "Frame" as it is called in the illustration). Each display can be given a name 1700, which is generally the name of the person that will be viewing the display. Next, is a way to specify the display's Time Zone 1710. Alternatively, time zone information can be obtained via the network that the display is connected to.

Some form of location description, such as city or room number can be specified next 1720. The combination of display names and location help to uniquely identify each display.

If it is OK for this display to accept Group Messages, a checkbox 1730 is provided for doing so. This checkbox is automatically checked when the Master User clicks on the email invitation 830, but can be subsequently unchecked or rechecked at any time.

Figure 18:
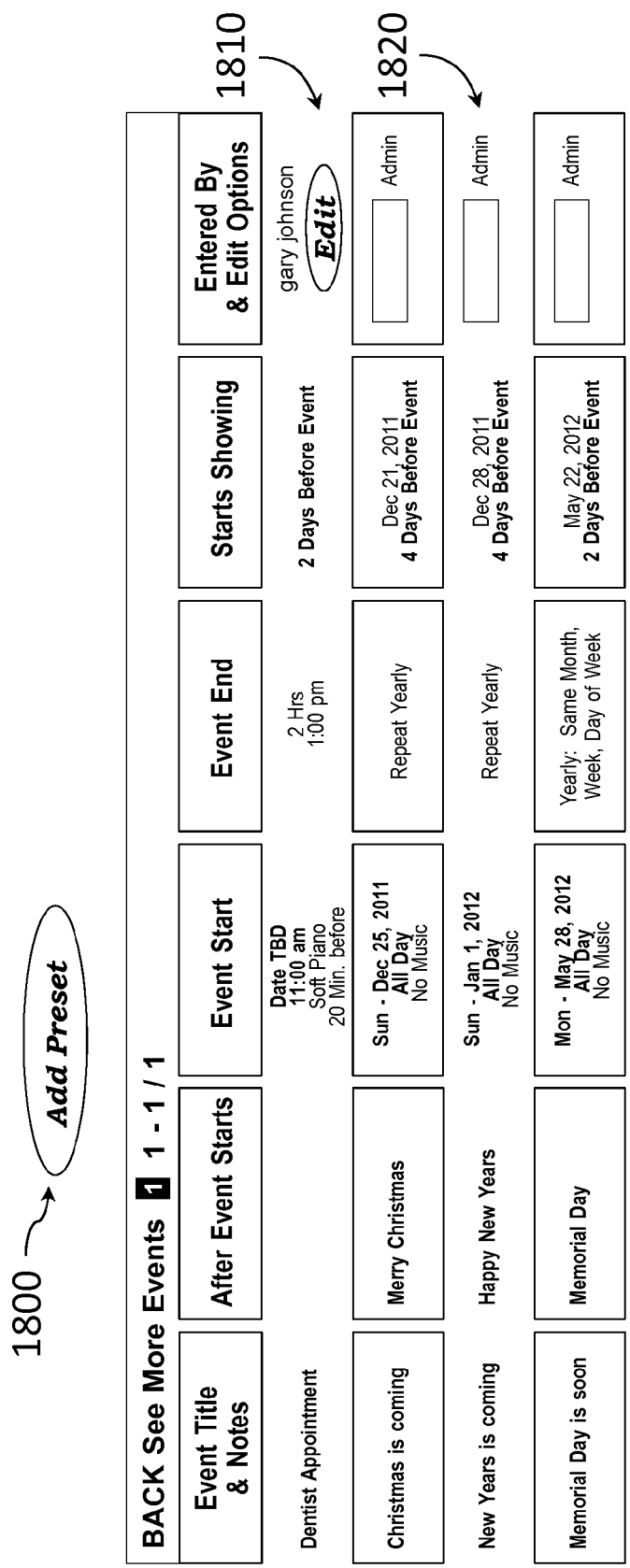
FIG. 18 illustrates an example user interface showing existing preset reminders.

FIG. 18 shows an interface for managing Preset reminders. Some preset reminders are defined by the system and are shown here as coming from Admin 1820. Some presets might have been defined by a Master User, normal User or Group User. If the user has edit privileges (which follow rules similar to regular reminder messages), an edit button will appear 1810.

Figure 19:
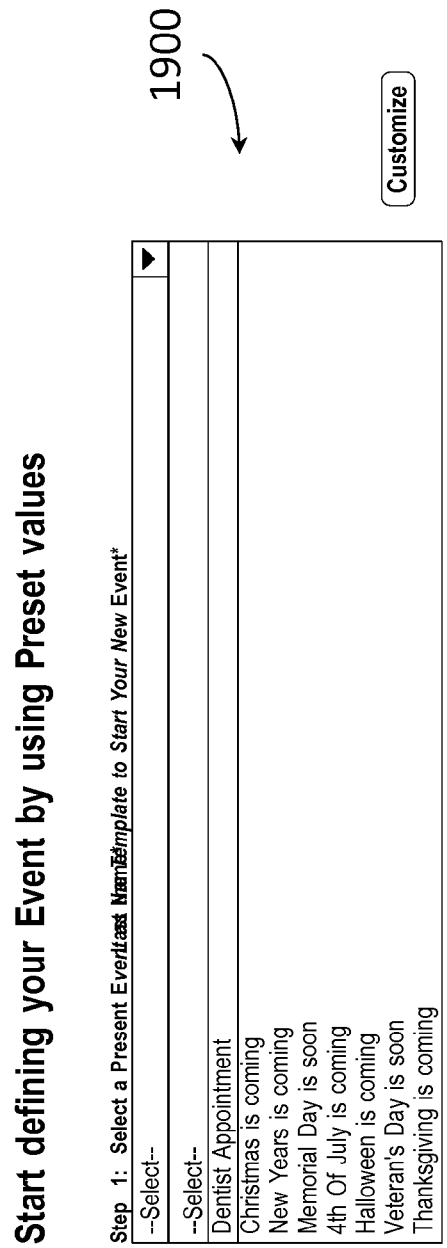
FIG. 19 illustrates an example user interface for selecting a preset reminder

FIG. 19 shows a simple way for picking a Preset. Once Presets have been defined, they are available for picking 1900 when creating a new reminder message by clicking on a button for Presets (not illustrated, but it would be found on an interface similar to that shown in FIG. 11). Once a Preset is selected, it can be subsequently modified and customized. Thus, users are not locked into a particular set of parameters, dates, times, etc.

Figure 20:
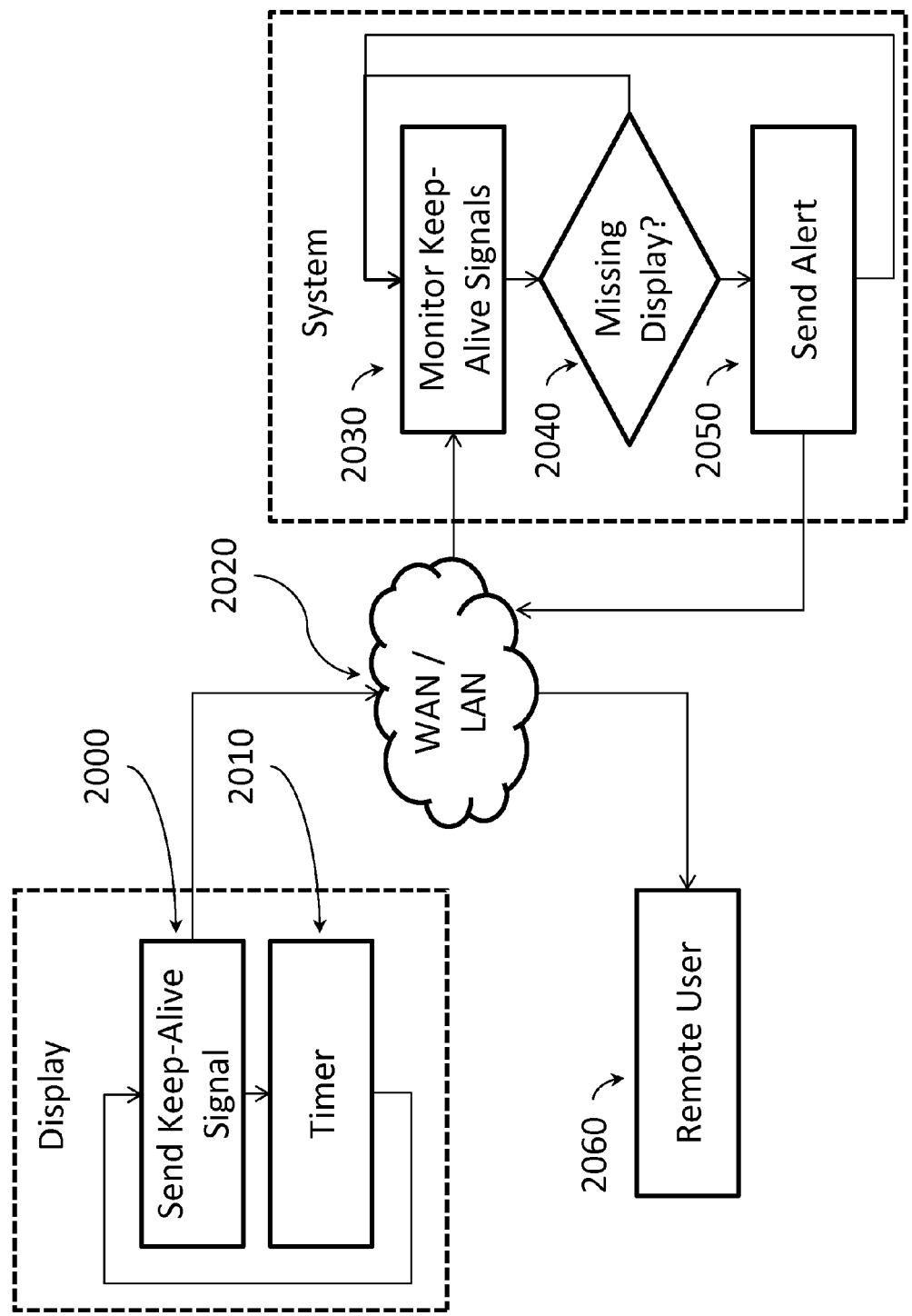
FIG. 20 is a diagram for showing how a display device's health can be monitored

FIG. 20 shows a low-level operation designed to monitor the health of a given set of displays. Displays can be accidently turned off, lose power or communications, or have a hardware failure. Since the display is usually not near the people that manage it, there needs to be a way to get some indication about its health.

To do so starts with the display sending out a periodic "keep-alive" signal 2000 to the server via the network 2020. The frequency of this keep-alive signal can be preset 2010 and does not need to be too frequent, depending upon needs.

The server ("system" in this illustration) accepts the keep-alive signals from all of the displays that it is monitoring 2030. If one or more of the displays fails to send a keep-alive signal 2040, an alert can be sent 2050. Alternatively, a webpage can be updated to show the suspect display name and location.

Meantime, Users 2060 can view the status of the display and/or receive alerts even though they are nowhere near the display.

Figure 21:
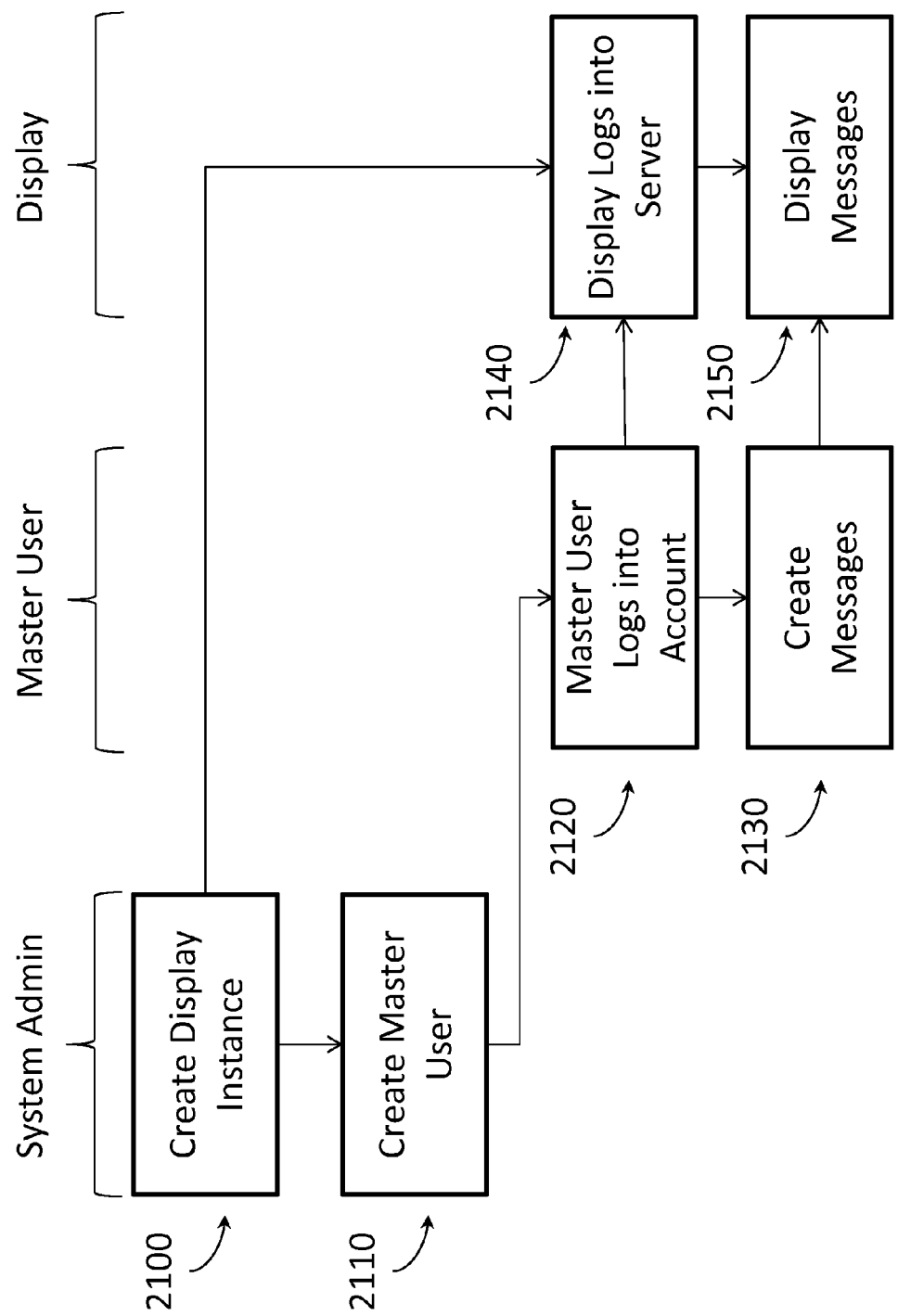
FIG. 21 depicts the display and master user setup.

FIG. 21 shows another low-level admin function, display and Master User setup.

For each display a unique account needs to be created. This account can be created by a system administrator 2100. This administrator can be a service provider or someone at a factory. If the display is a unique device made specifically to work in this system, a unique account code, probably algorithmically generated, can be stored in the display's nonvolatile memory. If a service provider is creating the display's account, any number of means may be used to create unique codes. Once created, these unique account codes are also stored in the system database 160, 505.

Next, the system administrator creates a new Master User account. This account consists of a unique username and a pointer to a specific display. A password, advisably unique, is also generated. Again, if the display is made specifically with this system in mind, the Master User setup can be done in the display's factory. Alternatively, a service provider can create the Master User account details. Either way, once created, this information is also stored in the same database 160, 510.

Next, the new Master User is given the new username and password. This Master User then logs into the system 2120. Once logged in, this person can create new reminder messages 2130, create other users, etc., as described earlier.

Before or after this step the Master User installs the display where it is intended to be used (e.g. the person with Alzheimer's). Installation consists of logging the display into the system 2140. Logging into the system involves two steps. The first step is to establish a network connection. This connection can be accomplished in a number of ways depending upon the specific type of network connectivity used. Connectivity can be accomplished via various wired (e.g. LAN via a cable, modem via phone) or wireless (e.g. Wi-Fi, cellular, Bluetooth) means. For example, if there is an existing Internet service available via a Wi-Fi connection, the display would first need to establish a link to this Wi-Fi.

The second step for logging the display into the system is to make the system aware of the display's unique identification code established earlier 2100. This step can be done manually or automatically by the display.

If done manually a screen on the display would ask for the display's account log in information, such as a username and password. The user could use any of a variety of input devices (e.g. touchscreen, remote control or keyboard) to enter the required information.

If done automatically, the display would read its unique identification information from nonvolatile memory and pass this information to the system. Automatic logging in of the display can be done once the display's nonvolatile memory is loaded with the required information, either by the factory or the Master User.

Password, in particular, would be encrypted before being passed to the server. Encryption is necessary to preserve privacy.

FIG. 22 shows a prototype display device. It is in a stand so that it can be placed on a tabletop. Alternatively, such a display can be built into a wall or be part of another device, such as a television.

Notice that similar to FIGS. 2 and 3, messaging is tailored to fit the current time relative to each event. For example, "Dinner with Jerry" is shown as "In 2 Days" 2210, which is a Tuesday at 6 PM 2215. The birthday is "In 3 Days", and since this is an All-Day event, no time of day is given—it just says it is on "Wednesday" 2220.

A "Visit Alice" event shows a bit more detail 2230. This happens to be a multi-day event, so we see that it starts "In about a Week" on "December 17" and lasts "For 3 Days" 2235.

Each of these messages will automatically change over time, depending upon how close to the event it is, and if the event has started, or just ended.

The illustrated sample display has a white background because the photo was taken during the day. To reduce the possibility of disturbing someone's sleeping, during night hours the display's background becomes black and font colors are adjusted accordingly for readability. Timing for when the display goes into night mode can be arbitrary, set by Master User selected options, or automatically adjusted according to where in the world the display is located, as determined by the geo-location of the IP address detected by the display.

Figure 33:
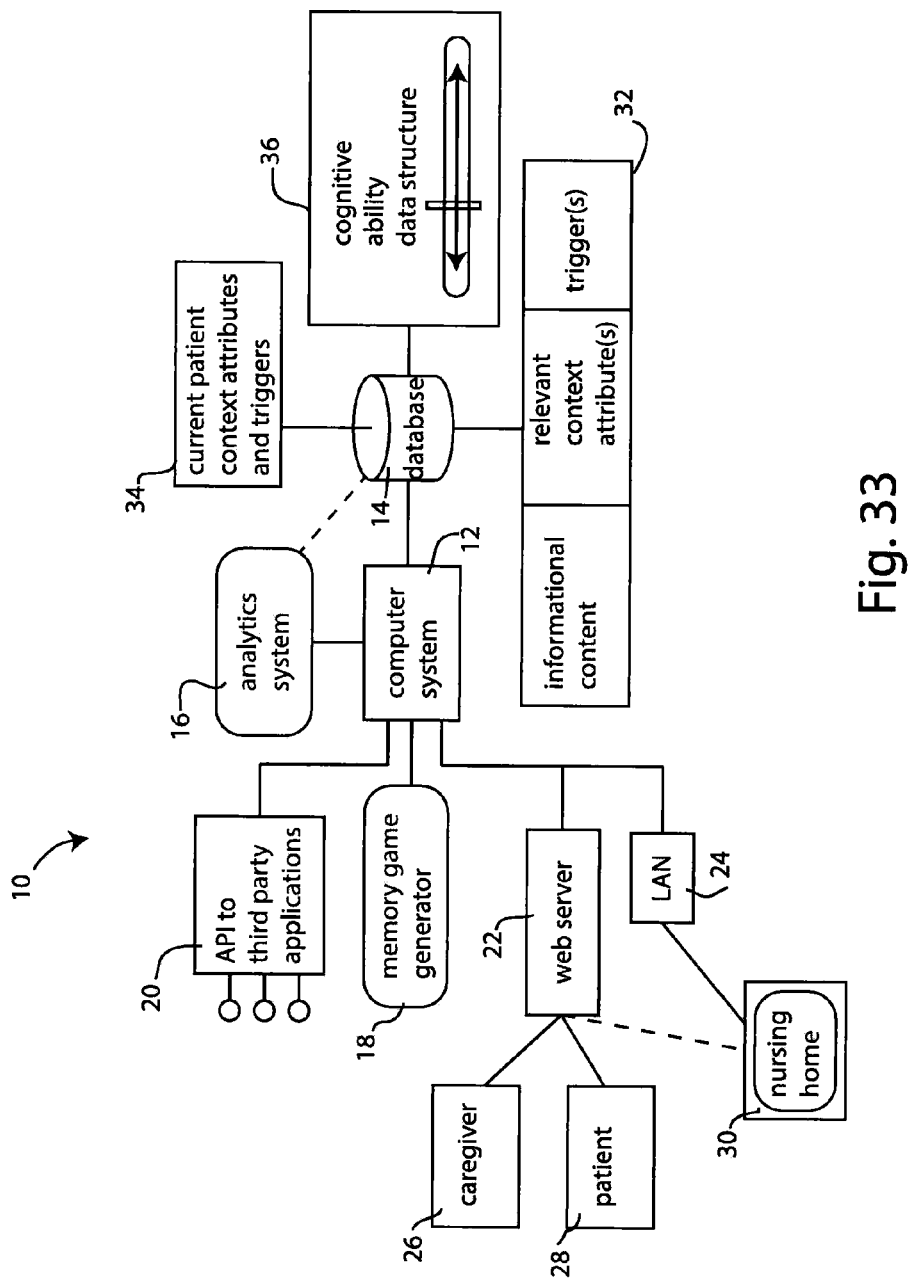
FIG. 33 is a block diagram showing the computer-implemented system and its associated database and data structures.

Referring now to FIG. 33, a computer-implemented system for assisting persons of reduced cognitive ability to manage upcoming events will now be discussed. The computer-implemented system is shown generally at 10, and includes a computer system 12, which may be implemented using a single computer or using a networked group of computers to handle the various functions described herein in a distributed fashion. The computer system 12 manages an electronic database 14 and also optionally an analytics system used to analyze data stored in the database 14. The database 14 functions as a data store configured to store plural items of information about time-based events (and other context-based events) for the patient. The analytics system may be programmed, for example, to analyze trends in a particular patient's cognitive abilities, so as to adjust the performance of the system to match those abilities, and also to provide feedback information about the patient to interested parties such as the patient's caregiver.

If desired several different presentation devices may be used by a single patient. For example, one device may be a tablet computer operated by the patient, while another device may be a wall-mounted television display in the patient's room. The system can dynamically control which device to use to interact with the patient. In some instances both devices may be used simultaneously. The system is able to customize the presentation sent to each device individually. Thus the level of complexity for the television display might be different than that used for the tablet computer, in a given situation. The system is able to use context information and also the patient's cognitive ability to adapt each display as appropriate for the patient's needs.

The computer system 12 may also be programmed to generate memory games that are supplied to the patient. Thus a memory game generator 16 is shown as coupled to the computer system. It will be understood that the generator may be implemented by programming the computer system 12 to generate and make available the appropriate memory games, based on the patient's cognitive ability. Memory games can be extremely helpful to exercise the patient's memory, possibly slowing the progress of the patient's disease. In addition, feedback information captured automatically as the patient plays the game is used to gather information about the patient's current cognitive ability, which is used by other systems as will be more fully explained below.

The computer system 12 also preferably includes an application program interface (API) that presents a set of standardized inputs/outputs and accompanying communications protocols to allow third party application developers to build software applications and physical devices that interact with the system 10, perhaps reading or writing data to the database 14.

The computer system 12 includes a web server 22 by which the caregiver 26 and patient 28 communicate with the computer system 12. In this regard web pages are delivered for viewing and interaction by computer devices such as tablets, laptop computers, desktop computers, smartphones and the like. The computer system 12 may also be connected to a local area network (LAN) 24, which allows other computer devices to communicate with the computer system 12, such as a workstation computer terminal utilized by a nursing home staff member 30, for example.

The database 14 is configured to store data organized according to predefined data structures that facilitate provision of the services performed by the computer system. The database includes a data structure 32 that stores plural items of information (informational content) that are each associated with a set of relevant context attributes and associated triggers. By way of example, an item of informational content might be a reminder message that the patient has an optometrist appointment. Associated with that message might be a trigger datum indicating when the appointment is scheduled. Also associated with the message might be other context attributes, such as how large the message should be displayed based on what device the message is being viewed upon. See FIG. 32 as an example of a display of this message.

When the appointment is still distant in time, the informational content stored for that event might include a very general text reminder, stored as one record in the data structure 32. As the time for the event draws near, the system might provide more detailed information about the event (such as a reminder to "bring your old glasses"). This would be stored as a second record in the data structure. The system chooses the appropriate item of information, by selecting the one that matches the current context.

In this regard, the system also stores in another data structure, the current context for the patient, such as where the patient is located, any relevant medical condition attributes, and the like. These are shown as context data structure 34. Further details of the context attributes are discussed below. The computer system 12 uses the current context attributes in structure 34 in determining which information content to retrieve from structure 32.

In addition to the patient's current context, the computer system further maintains a cognitive ability data structure 36 which stores data indicative of the patient's cognitive ability. This may be quantified, for example as a relative value suitable for representing as a sliding scale, e.g., a 1-10 scale. The patient's cognitive ability may be assessed by explicit entry by the caregiver or nursing home staff. Alternatively the system can establish the cognitive ability data itself through feedback from the memory game generator 18 or by analyzing how well the patient is able to interact with the system generally.

Figure 23:
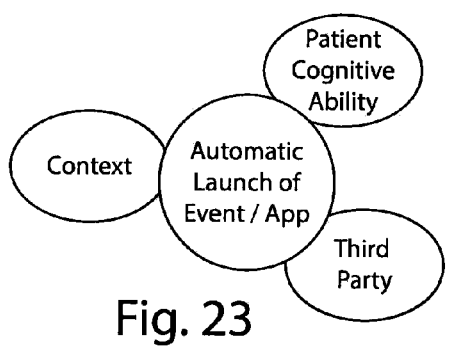
FIG. 23 is an entity diagram illustrating basic components of how an event or application is launched automatically using the disclosed system.

In one embodiment the system automatically launches specific applications and events based on set parameters configured by third parties, taking into account specific information, such as patient context, technology context, and situation context. FIG. 23 shows the key considerations that are taken into account during the process of determining which application/event to launch, when to launch it, and how to launch it. If the context information meets the parameter settings, the execution of an application and/or event is triggered. This provides some information or interaction for an individual to see or use on a computer terminal such as a tablet computer. The system also adjusts the level of interactivity based on the cognitive ability of the patient. The goal is to provide a patient or user a non-intrusive, automatic way to get information and services that are relevant and sometimes necessary.

With reference to FIG. 23, the third party is a person or entity that generally has at least some involvement in care giving. Such third party may have control to put in reminders, start videoconferences, upload pictures, set appointments, and other features of remote care. As used herein, the term "caregiver" refers to such a third party and may include family members, doctors, nursing staff and the like.

As depicted in FIG. 23, context also provides useful information. The system is able to initiate some of events/applications with knowledge of other factors that the care giver may not be aware of. These include the situation currently at the nursing home or other patient center (current situation detectable by cameras, microphones, nurse/doctor input, medical sensors, and the like), active/available technology information (e.g. don't send the reminder to the person's watch but put it on the TV), and medical information (data from medical sensors, current doctor reports, current status reports by users.

Cognitive Ability

Patient cognitive ability also forms an important aspect of the system, as shown in FIG. 23. Patient cognitive ability is the current level (on a rating scale) of the patient's ability to interact with the electronics system, tablet, or other device in the system. If the rating is high, the patient likely can interact with the device himself or herself and may not need as much assistance from some context or third party support. If the rating is low, the system and third parties can provide more support. Cognitive ability scale, and how it is determined, is discussed more in relation to FIGS. 29 and 30 below.

The computer-implemented system captures and stores an electronic data record indicative of the patient's cognitive ability. In one embodiment the electronic data corresponds to a collection of individual measurements or assessments of skill (skill variables), each represented numerically over a suitable range, such as a range from 0 to 10. If desired, an overall cognitive ability rating or aggregate assessment may also be computed and stored, based on the individual measurements or assessments.

The dynamic rendering system uses these skill variables to render facts in the most appropriate manner based on the patient's skill set. In this embodiment the collection of skill variables, stored in memory of the computer, thus correspond to the overall "cognitive ability" of the patient.

The skill variables comprise a set that can be static or dynamic. Some variables are measured or assessed by human operators and some are automatically assessed by the system based on historical observations and sensor data. The following is a list of the skill variables utilized by the system. In this regard a system may not require all of these variable, and likewise there are other variables, not listed here, that are within the scope of this disclosure as would be understood by those of skill in the art.

Anxiety level
Vision impairment or Skills
Short term memory skills
Long term memory skills
Recognizing and remembering names/familiar faces
Reading comprehension skills
Attention skills
time and space sensing
Speech skills
Hearing and comprehension skills
Ability to solve simple logical problems
Inference skill (ability understand normal implied consequences of actions and facts)

Figure 24:
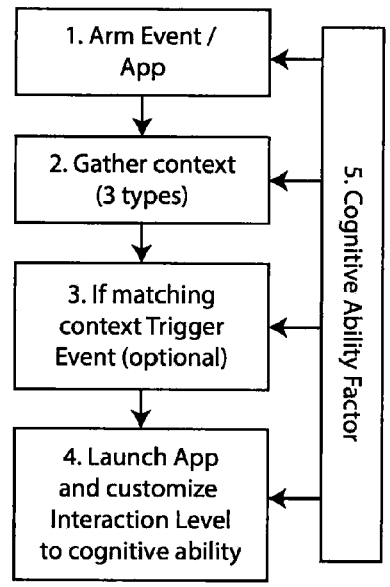
FIG. 24 is a high level flowchart diagram illustrating how cognitive ability factors into the launching of an event or application.

If desired, these skill variables may be algorithmically combined by the computer system to derive a single value "cognitive ability" score. A suitable scoring mechanism may be based on the clinically recognized stages of Alzheimer's disease, namely:
Stage 1: No impairment
Stage 2: Very mild decline
Stage 3: Mild decline
Stage 4: Moderate decline
Stage 5: Moderately severe decline
Stage 6: Severe decline
Stage 7: Very severe decline Context In addition to cognitive ability, the system also takes contextual information relevant to the patient into account. FIG. 24 shows the high level flow chart for this context-dependent application/event activation for people with various cognitive abilities. (Step 1) A third party (e.g. family, friend, caregiver) will input information and configure the parameters for triggering of events and applications. (Step 2) Once the system has been armed, the system will gather and store contextual information. Such context information, about events and the like, are preferably composed of three sub-contexts: patient related information, situational/external information, and event/application/device information. (Step 3) If contexts meet the armed settings of the system, an event may be triggered. (Step 4) If triggered, the system will launch the application whilst customizing the interaction level for the patient.

In one embodiment the context of an event (an event being an application, task, etc.) can be composed of 3 sub-contexts: a patient-related context, a situational or external condition context, and a technology context. The state of these contexts are stored in a context data structure within the memory of a computer forming part of the system.

The Patient-Related Context

The patient related context contains all the information that is available from the patient including (this is not exclusive). This information is stored as data in the context data structure. Examples of patient-related context data include:
Medical context obtained from sensors (e.g. vital signs)
Digital medical record (history)
Patient behavior (e.g. sleeping or not)
Patient location (e.g. in the room, looking at the display)
Patient preference (e.g. audio trigger/notification preferred, preferences of sounds, videos, tv shows, pictures)
Family/Caregiver wishes The Situational or External Condition Context The situational/external context contains all the information that is available from external sources to the patient (this is not exclusive). This information is likewise stored as data in the context data structure. Examples of situational or external condition context data include:
Weather information
Time
Third party(ies) information (e.g. identity)
Watching TV and what's on
Other people are in the patient room The Technology Context The Event Application/Device context contains all the information that is available from the devices that make up the system. This information, collected by communicating with the devices themselves, is likewise stored as data in the context data structure. Examples of technology context data include:
Status of the tablet display device
Amount of bandwidth available Type of display (e.g. size)
Type of network
Other devices available (smart watches, TV's in the room, other components in the system)

The technology context is useful because different devices may be added to the network at a future time to add additional functionality. For example, if the patient or patients caregiver purchased a 'help me' necklace, or a new TV, or a digital picture frame, the system can recognize contexts including these new technology (allowing the system to modify its behavior, for example, by displaying the pictures on the picture frame instead of the master tablet device.

Each event/application uses a specific context (subset of the most general context) to be triggered.

Polling Contextual Information

Figure 25:
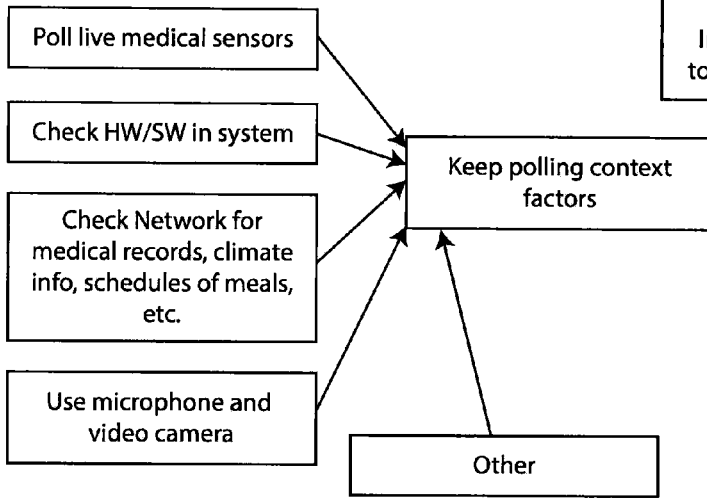
FIG. 25 is a flowchart depicting how context is gathered and used by various components within the system.

FIG. 25 illustrates the polling contextual information that the system will gather from Step 2 of FIG. 24. As previously mentioned, the information will be divided into three categories. Patient related information such as medical records will need to be manually inputted into the system database by a third party. However, live medical information will be constantly gathered by the system via sensors, stationary and mobile.

Figure 26:
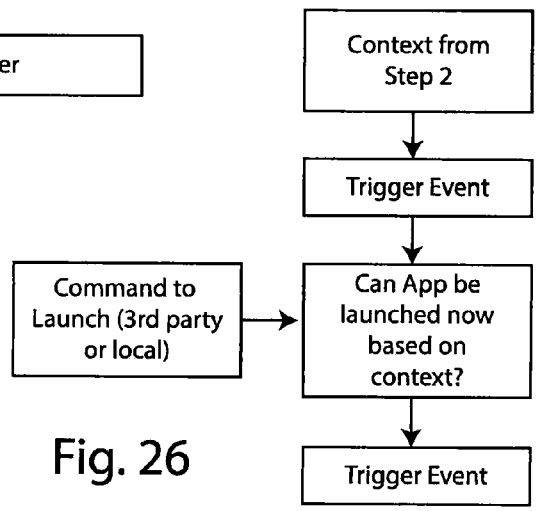
FIG. 26 is a flowchart illustrating the trigger event flow implemented by the system.

Once all contextual information has been gathered, the system will analyze the data to determine whether an event will be triggered based on the parameters set by the third party (FIG. 26). If it is determined that the trigger contexts have been met, then the system will evaluate whether the event will be launched. For example, if the schedule reminder is to go off at a specific time, the system will need to determine whether the patient is present in the room. If the patient is not in the room, the system will not launch the alert; however, if the patient is observed to be present, then the system will trigger the event. Similarly the system will not launch the alert or event when, for example, a family member wants to engage in a video call, but the context indicates that it is nap time, or that a doctor is currently doing therapy (based on a priority ranking). Likewise the system would not launch a reminder about medication if the patient is still at dinner and the medication is to be taken after dinner.

Figure 27:
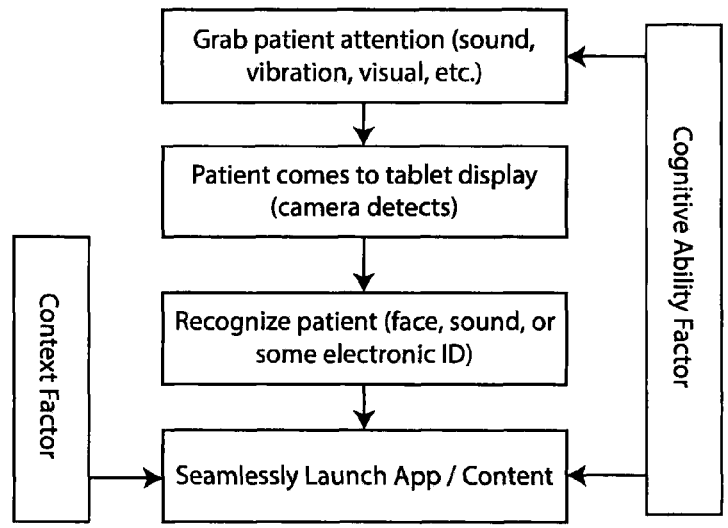
FIG. 27 is a flowchart illustrating the event launch flow implemented by the system.
Figure 28:
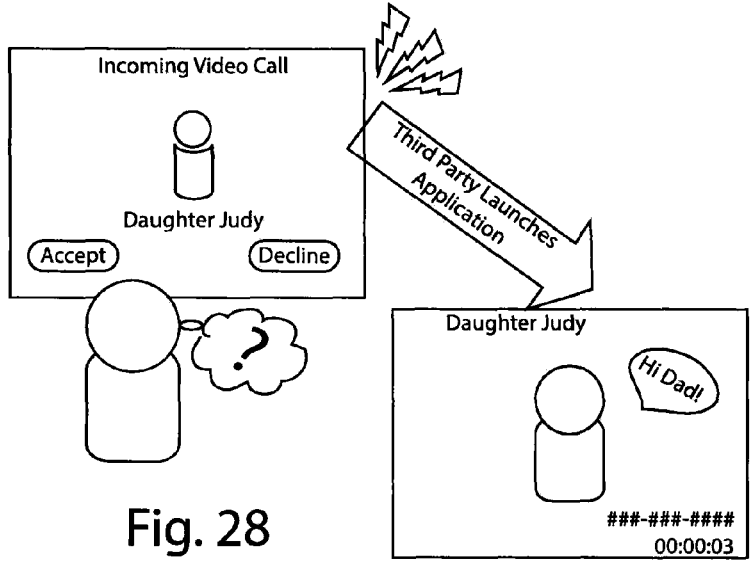
FIG. 28 is a use case diagram showing an exemplary use of the system.

Other examples of trigger events include:
person falls
timed event (e.g. medication/reminder)
sleeping, eating, blood pressure
third party initiation
another person enters room
voice command As shown in FIG. 27, depending on the patient's cognitive ability, the method of obtaining the patient's attention may be more obtrusive and obvious. The alert will draw the patient towards the tablet display screen, at which time the camera will detect the presence of the patient. If the presence is recognized as the patient (identification may be established by facial recognition, sound or other electronic identification system), the system will seamlessly launch the application/content. Upon launch of the event, the system will again consider the cognitive level of the patient to adjust the level of interactivity and necessity for interpretation appropriately. For example, if the patient is receiving a video call, then the system will alert the patient. if the patient is fully functional, the system will display the options for the patient to either accept or decline the video call. In the case of a low cognitive patient, the system will authenticate the patient's identity prior to automatically launching the video call or the calling third party could automatically initiate the application, as shown in FIG. 28.

Figure 29:
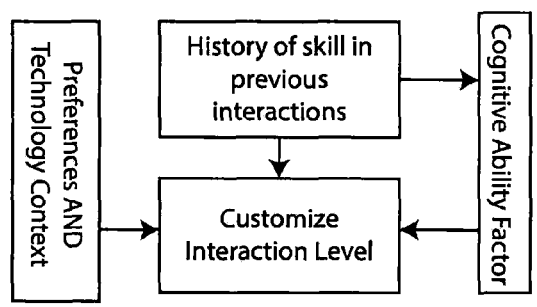
FIG. 29 is an interaction diagram showing how the interaction level of the system is customized based on cognitive ability and based on preferences and technology context information.

When customizing the interface for the patient, the system will take into consideration several factors (FIG. 29). Initially, the cognitive ability of a patient will need to be inputted manually by a third party; however, as the patient continues to utilize the system, the system will register and adapt to the history of skills of the patient from pervious interactions. The system also can provide mini-games specifically designed to test the current cognitive ability and thus the system can automatically update how it should interact with the user.

Figure 30:
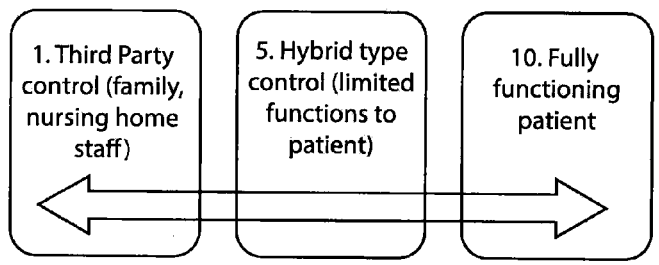
FIG. 30 is a diagram showing how cognitive ability is modeled by the system, as reflected in the cognitive ability data structure maintained in computer memory by the system.

Additionally, the system will apply the preferences of the patient and third party individuals (e.g. doctors, caregivers, family, friends, etc.). Thus, the patient will not have difficulties using or interpreting the system's events. The interface of the system will change depending on the patient's preferences and cognitive level as well. From a simple and automatic interface for those who are cognitively (or technological) incapable to more complex and manual for the independent and cognitively high leveled patient (FIG. 30).

Adjusting the actual use of applications (not just launching the application but also changing the user interface, buttons and/or modes of interaction) based on determined cognitive ability factor is important to making sure that the application can be useful to the patient.

One embodiment requires manual input of the patient's cognitive level; however, the system will adapt to the patient by having the patient perform tests within the system. The embodiment may be configured to day-to-day differing cognitive levels. The systems parameters can be routinely adjusted by third parties. Alternatively the system can be configured to perform daily or weekly or bi-weekly testings to automatically accommodate the patient's needs.

Customization of the system is not limited to events launched when contexts are triggered. The system may launch events when in a state of rest. For example, if there are no events set to launch, yet the patient is observed to be present in the room, the system tablet display may go dark or display a picture show or become a reflective mirror.

Figure 31:
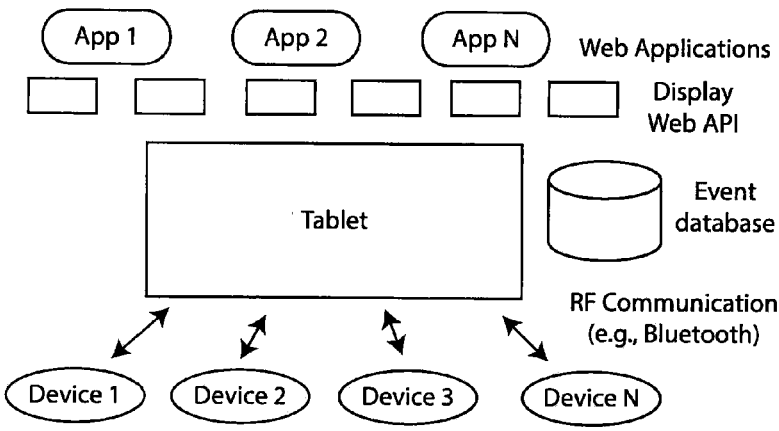
FIG. 31 is a block diagram showing one tablet-based, web-enabled system embodiment.
Figure 32:
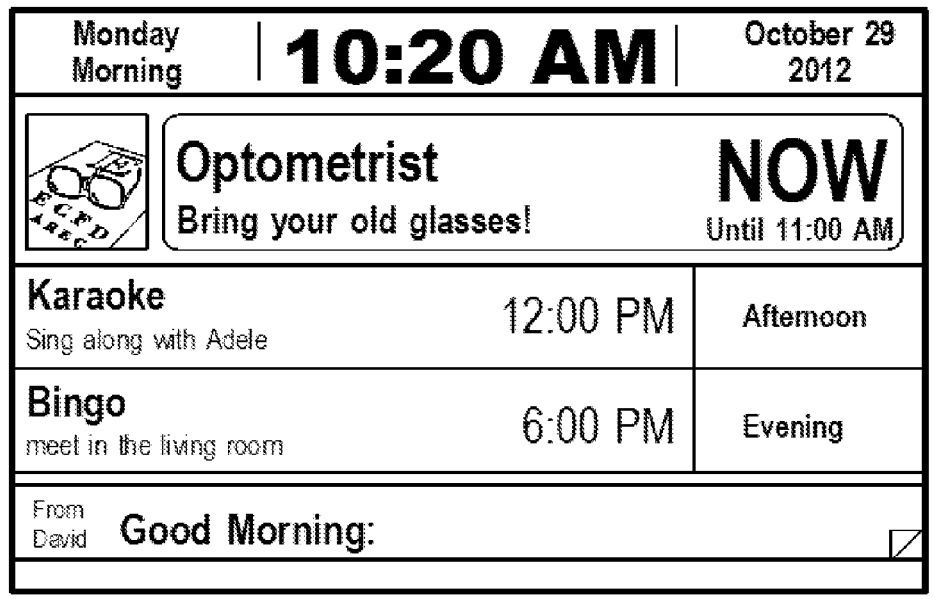
FIG. 32 shows an example screen display with several exemplary applications/events launched.

FIG. 31 illustrates one embodiment in which the system is comprised of the tablet screen, event database, multiple web applications, RF communication (e.g. Bluetooth), and connections to a multitude of devices (e.g. camera, microphone, speaker, computers, mobiles, etc.). The system will also display Web API. FIG. 32 shows an example user interface that includes applications/events that were launched.

If desired an additional display can be provided to the caregiver or to another third party. This additional display could be implemented on a tablet or smartphone and would provide information to the caregiver about what the patient is up to and activities he or she did in the past, as well as feedback about the patient's medical condition. This feedback loop provides reassuring information to the caregiver. In general use, this additional display presents information that is different from the information displayed on the device used by the patient. Like the information presented to the patient, the information presented to the caregiver is derived from information stored in the database system, which may be supported by a server associated with a nursing home or healthcare provider, or which may be supported by a service provider offering the services using Internet-based or cloud computing resources.

Additional Explanatory Use Cases

To further illustrate some of the possible uses of the disclosed system, consider the following use cases that are made possible by the disclosed computer-implemented system:

Video Communication initiated by remote third party which is launched when the patient is looking at the display. The attention of the patient can be triggered by an audible signal to bring the patient to the display Application triggered by a medical condition based on readings from devices connected through Bluetooth communication (e.g. message to the patient display if the readings show that he is dehydrated)

Application triggered by the understanding of patient behavior (e.g. patient in the room and not sleeping)

Activation based on a certain time of the day

Message displayed on a display depending on external conditions (e.g. based on finding that it is cold outside could warn the patient to wear a warm jacket or emergency message and what to do could be displayed in case of fire)

Pictures displayed on display if the display does not display other information (thus technology context shows no conflicts and patient context shows time of the day that the person may enjoy pictures)

Priority and Conflict Resolution

When several application are armed conflict can happen when several contexts are met at the same time. To solve this issue each application/event is assigned a level of priority. In case of same priority the one first entered in the queue is executed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented system for assisting persons of reduced cognitive ability to manage upcoming events, comprising:
    a computer-implemented data store configured to store information about a context-based event for a patient having reduced cognitive abilities;
    a networked computer system coupled to said data store that provides an information communicating interface to the patient;
    said computer system being programmed to monitor context information relevant to the patient, wherein the context information includes a time relative to the context-based event and wherein the context information includes information relating to at least one of: the patient's medical condition, weight, vital signs, activity level, habitual behaviors and lifestyle;
    said computer system being further programmed to dynamically adjust a presentation of said stored information to the patient based on said context information.

2. The system of claim 1 further comprising at least one sensor for measuring at least one of: the patient's medical condition, weight, vital signs, activity level, habitual behaviors and lifestyle.

3. The system of claim 1 wherein the context information includes information relating to at least one of: location of patient, mobility of patient and ambient temperature and weather conditions in proximity of patient.

4. The system of claim 1 further comprising at least one sensor for measuring at least one of: location of patient, mobility of patient and ambient temperature and weather conditions in proximity of patient.

5. The system of claim 1 wherein said context information is a patient-related context.

6. The system of claim 1 wherein said context information is a situational context external to the patient.

7. The system of claim 1 wherein said context information is a technology context associated with the networked computer system.

8. The system of claim 1 wherein said computer system being further programmed to dynamically adjust the presentation of said stored information by automatically launching an application running on the computer system.

9. The system of claim 1 wherein said computer system being further programmed to dynamically adjust the presentation of said stored information by automatically launching an application running on a device in proximity to the patient.

10. The system of claim 1 wherein said computer system being further programmed to dynamically adjust the presentation of said stored information by adapting the modality of a multi-modal device.

11. The system of claim 1 wherein said computer system being further programmed to dynamically adjust the complexity of information presented.

12. The system of claim 1 wherein said computer system being further programmed to dynamically adjust the content of information presented.

13. The system of claim 1 wherein said computer system includes a caregiver interface through which a caregiver furnishes information to said data store about time-based events for the patient.

14. The system of claim 1 wherein said computer system is further programmed to automatically transfer the presentation from a first device to a second device based on said context information.

15. The system of claim 1 wherein said computer system is programmed to present said stored information on a first device and a second device and further programmed to separately and dynamically adjust the presentation on said first and second devices based on said context information.

16. A computer-implemented system for assisting persons of reduced cognitive ability to manage upcoming events, comprising:
    a computer-implemented data store configured to store plural items of information about a context-based event for a patient having reduced cognitive abilities;
    a networked computer system coupled to said data store that provides:
        a first information communicating interface to the patient and
        a second information communicating interface to a caregiver associated with the patient;
    the data store having a data structure in which to store electronic data indicative of the patient's cognitive ability;
    the networked computer system being programmed to receive through said second interface plural items of information about a specific context-based event and being programmed to store said received plural items of information as a record in said data store associated with said specific context-based event;
    the networked computer system being programmed to dynamically render said stored information to the patient through the first interface in a manner such that the rendering changes as the context changes; and
    the networked computer system being further programmed to access said data structure storing said electronic data indicative of the patient's cognitive ability and to control the manner in which the dynamic presentation is delivered to the patient based on the accessed electronic data.

17. The system of claim 16 wherein the context-based event is a time-based event.

18. The system of claim 16 wherein the networked computer system is further programmed to collect interaction data from the patient through the first interface and to supply the collected interaction data to the caregiver through the second interface.

19. The system of claim 16 wherein the networked computer system is further programmed to collect information indicative of cognitive ability through the first interface and to store the collected information in the data structure storing electronic data indicative of the patient's cognitive ability.

20. The system of claim 16 wherein the networked computer system is further programmed to collect information indicative of cognitive ability and wherein the networked computer system is programmed to deliver a memory exercising game through the first interface and to extract from said game said information indicative of cognitive ability.

21. The system of claim 16 wherein the first interface is a display interface supported by at least one of a portable device and a wearable device used by the patient.

22. The system of claim 16 wherein the first interface includes a display screen and the electronic data indicative of the patient's cognitive ability is used to adjust the amount of information presented concurrently on the display screen.

23. The system of claim 16 wherein the first interface includes an aural interface producing speech messages and the electronic data indicative of the patient's cognitive ability is used to adjust at least one of speaking speed, vocabulary, and grammatical complexity of the speech messages.

24. The system of claim 16 further comprising a sensor measuring at least one of the patient's medical condition, weight, vital signs, activity level, habitual behaviors and lifestyle, location, mobility, ambient temperature and weather conditions in proximity of patient; and
wherein the networked computer system is programmed to adjust the dynamic presentation based on said sensor-measured condition.

25. The system of claim 16 wherein the plural items of information each provide successively greater amounts of information about the time-based event.

26. The system of claim 16 wherein said caregiver is a member of the patient's family and the second interface is supported by a browser running on a device operated by the caregiver and communicating with said networked computer system.

27. The system of claim 16 wherein said caregiver is a member of a professional nursing home or healthcare organization and the second interface is supported by a browser running on a device operated by the caregiver and communicating with said networked computer system.

28. The system of claim 16 wherein said caregiver is a member of a professional nursing home or healthcare organization and the second interface is supported by a client application running on a device operated by the caregiver and communicating with said networked computer system.

29. The system of claim 16 wherein the first interface employs a computer device operated by or in proximity to the patient, said computer device running an autonomous program that delivers said dynamic presentation even when communication with the networked computer system is interrupted.

30. The system of claim 16 wherein said first interface includes speech input responsive to speech of the patient and wherein said networked computer system is programmed to receive said speech input and use it to assess the cognitive ability or emotional state of the patient.

31. The system of claim 16 wherein the networked computer system provides a third information communicating interface to another caregiver who inputs information about the condition of the patient.

32. The system of claim 16 wherein the networked computer system provides a third information communicating interface to another caregiver who inputs information about the condition of the patient wherein the information input by the another caregiver is used to update the electronic data indicative of the patient's cognitive ability.

33. The system of claim 16 wherein the networked computer system provides a third information communicating interface to another caregiver who inputs information about the condition of the patient wherein the information input by the another caregiver is used to supply status information about the patient through the second interface.

34. The system of claim 16 wherein the networked computer system provides a software interface adapted to allow other software systems to interact with the data store.

35. The system of claim 16 wherein the networked computer system provides a software interface adapted to allow a sensor measuring at least one of the patient's medical condition, weight, activity level, habitual behaviors, lifestyle, location, mobility, ambient temperature and weather conditions in proximity of patient to interact with the data store.

36. The system of claim 16 wherein the data structure is configured to represent cognitive ability as a model corresponding to a set of dimensions including at least one of anxiety level, vision impairment, vision skills, short-term memory skills, long-term memory skills, recognizing and remembering names/familiar faces, reading comprehension skills, attention skills, time and space sensing, speech skills, hearing and comprehension skills, ability to solve simple logical problems, and inference skill including ability to understand normal implied consequences of actions and facts.

37. The system of claim 16 wherein said networked computer system is programmed to automatically adjust the message as the patient's cognitive ability changes, as reflected by said accessed electronic data.

* * * * *